US010481171B2

(12) United States Patent
Croquette et al.

(10) Patent No.: US 10,481,171 B2
(45) Date of Patent: Nov. 19, 2019

(54) AUTOMATED SAMPLE STORAGE SYSTEM HAVING STORAGE CONSUMABLE WITH SUB-OPTIMAL STORAGE DENSITY

(71) Applicant: Brooks Automation, Inc., Chelmsford, MA (US)

(72) Inventors: Etienne Croquette, Altrincham (GB); Robin Grimwood, Chelford (GB); David Andrew Harding, Lanchashire (GB); Chris Walsh, Lancashire (GB)

(73) Assignee: BROOKS AUTOMATION, INC., Chelmsford, MA (US)

( * ) Notice: Subject to any disclaimer, the term of this patent is extended or adjusted under 35 U.S.C. 154(b) by 125 days.

(21) Appl. No.: 15/410,606

(22) Filed: Jan. 19, 2017

(65) Prior Publication Data

US 2017/0205437 A1    Jul. 20, 2017

(30) Foreign Application Priority Data

Jan. 20, 2016 (EP) .................................. 16275011

(51) Int. Cl.
| | |
|---|---|
| *G01N 35/04* | (2006.01) |
| *G01N 35/02* | (2006.01) |
| *B01L 3/00* | (2006.01) |

(52) U.S. Cl.
CPC ........... *G01N 35/04* (2013.01); *G01N 35/026* (2013.01); *G01N 35/028* (2013.01);
(Continued)

(58) Field of Classification Search
CPC ................. G01N 35/04; G01N 35/026; G01N 2035/0418; G01N 35/028; B01L 9/06; B01L 2200/025
(Continued)

(56) References Cited

U.S. PATENT DOCUMENTS

| | | |
|---|---|---|
| 2004/0037679 A1 | 2/2004 | Sato et al. |
| 2005/0180895 A1 | 8/2005 | Itoh |
| 2012/0060520 A1 | 3/2012 | Collins et al. |

FOREIGN PATENT DOCUMENTS

| | | |
|---|---|---|
| EP | 1348485 | 10/2003 |

OTHER PUBLICATIONS

American National Standards Institute: "for Microplates—Well Positions", ANSI/SBS 4-2004, Jan. 27, 2006, pp. 1-13; XP-002630822.
(Continued)

*Primary Examiner* — Robert R Raevis
(74) *Attorney, Agent, or Firm* — Perman & Green, LLP; Colin C. Durham

(57) ABSTRACT

An automated sample specimen storage system including a tube holding microplate including a plate frame, a predetermined array of tube holding receptacles formed in the plate frame, the receptacles having a SBS standard pitch corresponding to the predetermined array, and being configured for holding therein sample store and transport tubes, each disposed so as to contain sample specimen in a sample storage of the storage system and to effect, with the sample tube, delivery from the sample storage to a workstation, the predetermined array of receptacles defining a volume capacity of the tube holding microplate, and each of the receptacles being shaped to conformally engage walls of the sample tubes and hold a respective one of the sample store and transport tubes, wherein the receptacles are arranged so that the tube holding microplate volume capacity defined by the predetermined array is an under optimum volume capacity.

19 Claims, 17 Drawing Sheets

(52) U.S. Cl.
CPC .. *B01L 3/50825* (2013.01); *G01N 2035/0406* (2013.01); *G01N 2035/0418* (2013.01); *G01N 2035/0429* (2013.01); *G01N 2035/0493* (2013.01)

(58) Field of Classification Search
USPC ............... 73/863, 864.24, 864.25, 864.91; 422/500, 503, 509, 560–562, 63, 65; 436/174
See application file for complete search history.

(56) References Cited

OTHER PUBLICATIONS

European Search Report, European Application No. 16275011, dated Jul. 14, 2016.

AUTOMATED SAMPLE STORAGE SYSTEM HAVING STORAGE CONSUMABLE WITH SUB-OPTIMAL STORAGE DENSITY

CROSS-REFERENCE TO RELATED APPLICATIONS

This application claims priority to and the benefit of European Application No. 16275011.1, filed on 20 Jan. 2016, the disclosure of which is incorporated herein by reference in its entirety.

BACKGROUND

1. Field

The exemplary embodiments generally relate to automated sample stores and, more particularly, to automated sample stores using tube racks that are input and output from the sample store.

2. Brief Description of Related Developments

Storage of samples, such as biological or chemical samples, may be stored in compartmentalized storage such as storage housings or modules that in cases may be automated to effect sample transport into and out of the storage housings or modules as well as within the storage housings or modules.

Generally samples are stored industry standard trays such as in sample trays or microplates having an SBS (Society for Biomolecular Screening) format. For example, referring to FIG. 2B, a 96 well SBS sample microplate 200P has an 8×12 array of sample tube holding receptacles 210P arranged with a 9 mm pitch X (see ANSI SLAS 4-2004 (R2012) (formerly recognized as ANSI/SBS 4-2004) and ANSI SLAS 1-2004 (R2012) (formerly recognized as ANSI/SBS 1-2004), both of which are incorporated by reference herein in their entireties). Generally the standard format SBS sample microplates 200P have a width W of about 85.48 mm and a length L of about 127.76 mm. The pitch or distance X between the centers of the tube holding receptacles 210P positioned within the standard format SBS sample microplate 200P is about 9 mm so as to be compatible with industry standard devices such as multi-tip pipettes, sample tube cap removal/replacement devices, 2D code reading devices, sample tube sealing/piercing devices, etc.

Generally sample tubes stored in the sample trays maximize the storage volume in the sample tube (and hence the storage density of the sample tray) by making the sample tube as large as possible within the constraints of the standard format SBS sample tray. For example, conventional sample tubes generally have an outside diameter of just under 9 mm (e.g. referred to herein as a 9 mm sample tube) and conform to a standard SBS microplate with tube receptacles having an optimized volume capacity (e.g. the diameter of the 9 mm sample tube is substantially the same as the pitch between the tube receptacles).

It would be advantageous to have sample trays with a standard SBS footprint and sample tube receptacles having sub-optimal sample storage density that effect an increase in a picking throughput of an automated storage system.

BRIEF DESCRIPTION OF THE DRAWINGS

The foregoing aspects and other features of the disclosed embodiment are explained in the following description, taken in connection with the accompanying drawings, wherein.

DETAILED DESCRIPTION

Figure 1A:
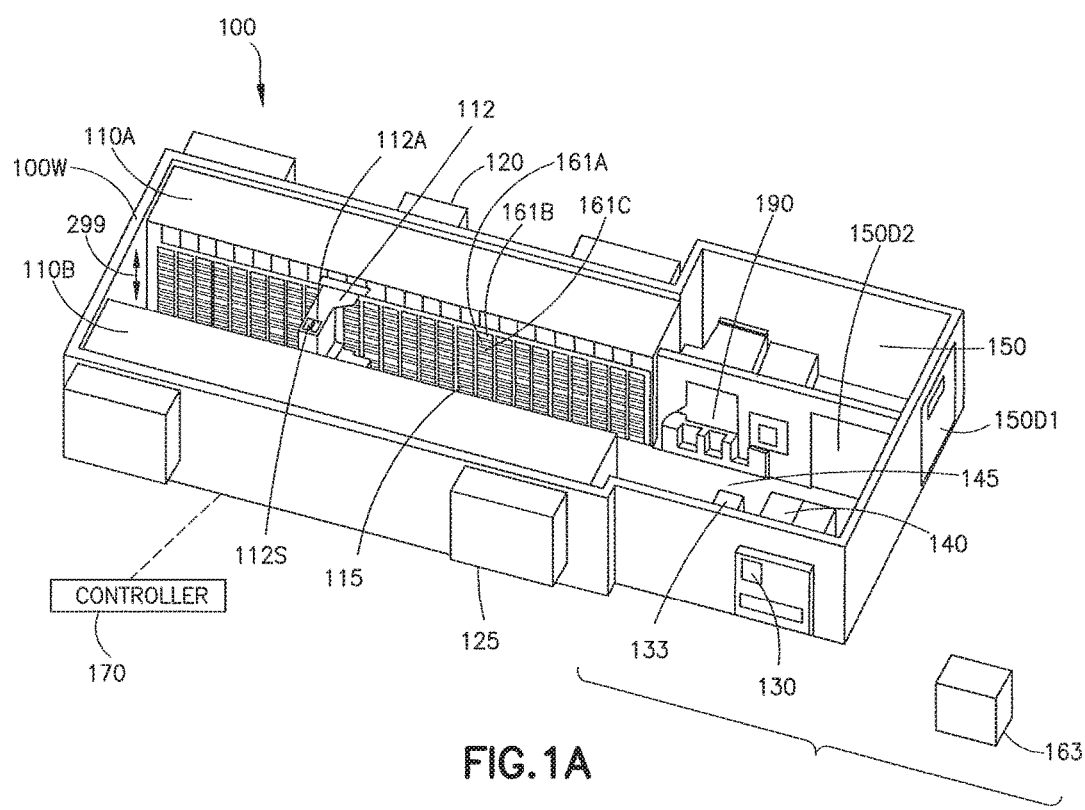
FIG. 1A a schematic illustration of a sample storage facility in accordance with aspects of the disclosed embodiment.

The aspects of the disclosed embodiment provide for increased picking throughput of an automated sample specimen storage system 100, 100' (also referred to herein as a sample storage facility or cold store) where sample store and transport tubes 250 (see FIG. 2C—also referred to as sample tubes) of the automated storage system are stored in trays having tube receptacles with a sub-optimal density, as will be described herein, with respect to a density of a standard SBS microplate having a standard SBS microplate pitch. The increased picking throughput of sample tubes 250 from the sample storage facility 100, 100' is provided for, as described herein, while maintaining an industry standard format for the sub-optimal or under optimum volume capacity microplates or trays 200 (see FIG. 2—as will be described herein, and also referred to as microplates 200) used to input and output the sample tubes 250 to and from the sample storage facility 100, 100'. FIG. 1A illustrates an automated sample specimen storage system/facility or cold store 100 (again referred to herein as the sample storage facility in accordance with aspects of the disclosed embodiment. Although the aspects of the disclosed embodiment will be described with reference to the drawings, it should be understood that the aspects of the disclosed embodiment can be embodied in many forms. In addition, any suitable size, shape or type of elements or materials could be used.

Figure 1B:
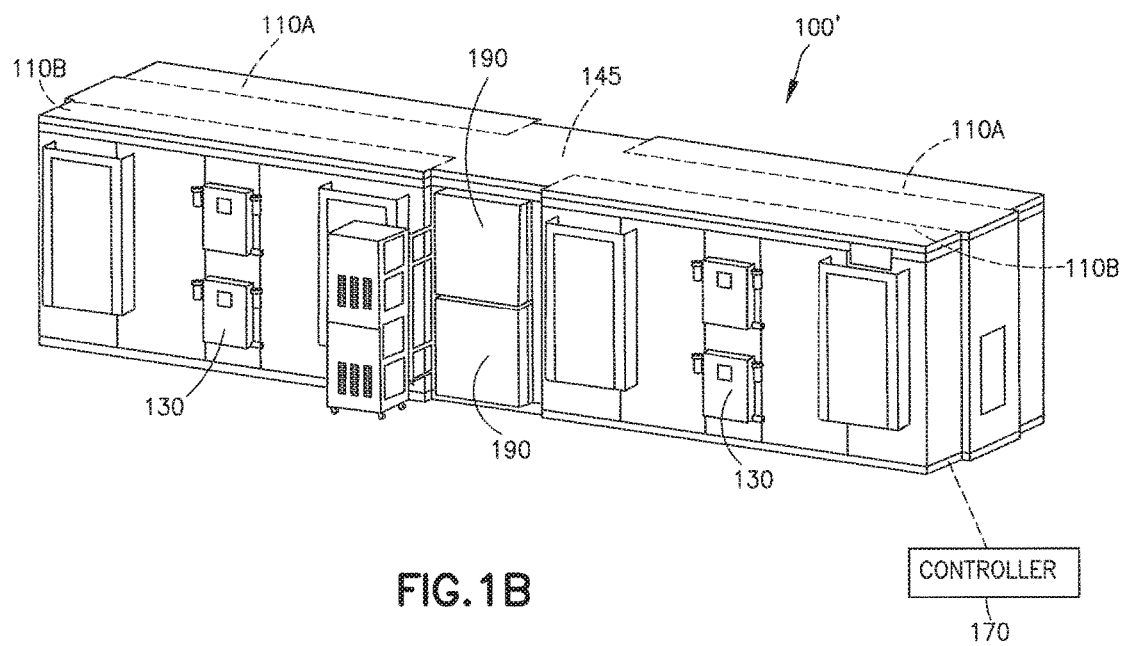
FIG. 1B is a schematic illustration of a sample storage facility in accordance with aspects of the disclosed embodiment.
Figure 1C:
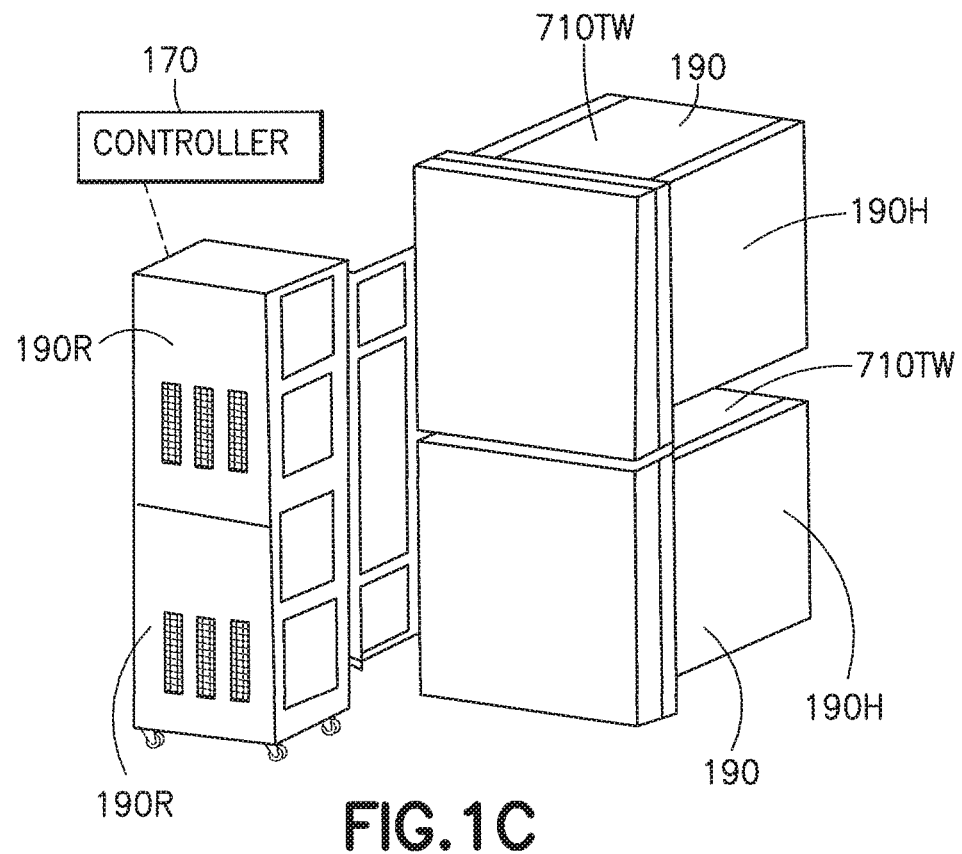
FIG. 1C is a schematic illustration of a portion of a sample storage facility in accordance with aspects of the disclosed embodiment.
Figure 1D:
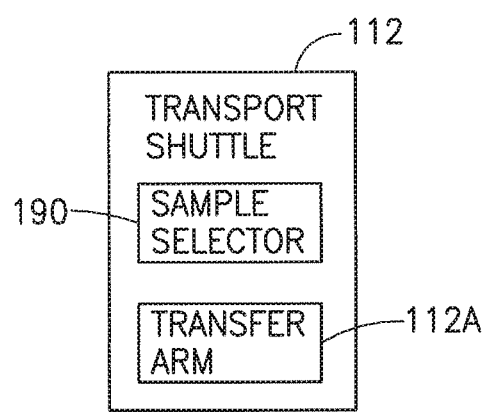
FIG. 1D is a schematic illustration of a portion of a sample storage facility in accordance with aspects of the disclosed embodiment.

The sample storage facility 100 may include any suitable number of environmental zones or areas that may be connected to one another. In some aspects the zones may have different environments and may isolated, otherwise the zones have a shared atmosphere. Storage facility 100 in the example shown in FIG. 1 is representative and in other aspects the storage facility may have any suitable arrangement. For example, the sample storage facility 100 may include one or more storage zones/areas 110A, 110B (also referred to herein as storage arrays 110A, 110B), a transport zone 145 and a climate controller antechamber 150. In other aspects the sample storage facility 100 may have any suitable number and type of zones/areas in which samples are stored and/or transported and which may be accessed by storage facility personnel. In one aspect, one or more panels/walls 100W may be removable to extend the storage capacity of the sample storage facility 100. In one aspect, the interior portions of the sample storage facility 100, such as the storage zones 110A and the transport zone 145 may be at any suitable temperature between room temperature and ultra-low temperatures (where the term "ultra-low temperature" shall mean temperatures below −50° C. and above temperatures generally considered to be cryogenic). In one aspect, the storage zones 110A, 110B and the transport zone 145 may be at temperature between about −20° C. and about room temperature. In other aspects, as illustrated in FIG. 1G, the sample storage facility 100 may be any suitable sample store, such as the SampleStore™ II available from Brooks Life Science Systems (the features of which are incorporated by reference herein) where the storage zones 110A, 110B may not have closures so that each storage location is open to the transport zone 145.

In one aspect the transport zone 145 may include an input/output module 130, a transport shuttle 112 and one or more sample selector modules 190 where the sample selector modules are disposed at least partly within the transport zone 145 as will be described below. The input/output module 130 may allow transfer of samples and/or sample trays to and from the sample storage facility 100 while maintaining a predetermined temperature within the transport zone 145. In one aspect, the input/output modules 130 are in communication with a storage area 140 (also referred to herein as storage array 140) of the sample storage facility 100 where storage area 140 is formed/defined by sub-optimal or under optimum volume capacity microplates or trays 200 (see FIG. 2) having a standard SBS footprint and a standard SBS spacing between tube holding receptacles as described herein. In other aspects, as will be described herein, at least a portion of the storage areas or arrays 110A, 110B may be formed/defined the sub-optimal or under optimum volume capacity microplates or trays 200 such as when the sub-optimal microplates 200 are placed within the storage areas or arrays 110A, 110B. The sample selector modules 190 may provide sorting capability for moving samples/sample holders 250 within or between the sub-optimal microplates 200 and/or high density/capacity (HD) sample racks/trays 370 (see FIG. 3). The sample selector modules 190 may be substantially similar to those described in U.S. patent application Ser. No. 14/229,077 filed on Mar. 28, 2014, the disclosure of which is incorporated by reference herein in its entirety. In one aspect, the sample selector modules 190 form part of a sample transport/picking chain or path between (e.g. to or from) the storage zones 110A, 110B and the sample storage area 140 formed by the sub-optimal microplates 200 as described herein.

The transport zone 145 may be maintained at any suitable low temperature, such as about −20° C. to about room temperature, in which a transport shuttle 112 and/or other automation may operate to transfer sample trays 200, 370 between the storage zones 110A, 110B, the sample selector modules 190 and the input/output module 130. In one aspect, the transport shuttle 112 may interface with a tile wall 115 where each tile (such as e.g. tiles 161A, 161B, 161C) is arranged to create, for example, a robotically friendly insulating closure of the storage zones 110A, 110B for removing sample trays, such as sample trays 370 and/or sample trays 200, from the storage zones 110A, 110B (in any suitable manner) through respective sealable or otherwise closable input/output openings sealed by a respective tile 161A, 161B, 161C. In one aspect, both the sample trays 370 and the sample trays 200 are stored in one or more of the storage areas 110A, 110B while in other aspects, only the sample trays 370 or the sample trays 200 are stored in one or more of the storage areas 110A, 110B. For example, in one aspect, the sample trays 370 may not be used such that only the storage trays 200 are stored in one or more of the storage areas 110A, 110B. Where the sample trays 200 are stored in the storage areas 110A, 110B the storage trays 200 may provide quicker access to frequently needed samples (compared to accessing samples in the sample trays 370) and/or provide for temporary (such as temporary overnight storage or temporary storage having any suitable time period) of samples. Suitable examples of sliding tile closures can be found in, for example, U.S. Pat. Nos. 7,635,246; 7,648,321 and 7,793,842; and U.S. patent application Ser. No. 13/595,817 filed on Aug. 27, 2012 and U.S. patent application Ser. No. 13/334,619 filed on Dec. 22, 2011, the disclosures which are incorporated by reference herein in their entireties. In one aspect the tiles 161A, 161B, 161C may be foam bricks or blocks that are arranged to create, for example, the robotically friendly insulating closure. In other aspects, the tiles 161A, 161B, 161C may be constructed of any suitable material and may interface with any suitable automation and/or personnel for opening and closing a respective input/output opening in any suitable manner. In one aspect, the tiles 161A, 161B, 161C may be held in place (e.g. in a closed position) by gravity or in any other suitable manner. Guide rails on each side of a respective tile may constrain the tiles against lateral movement while allowing them to slide up and down freely in the direction of arrow 299 for opening and closing a respective input/output opening. In one aspect, any suitable automated transfer mechanism of the sample storage facility 100, such as transport shuttle 112, may insert or remove a sample tray, such as high density tray 370 (FIG. 3) to or from the isolated climate controlled storage zones 110A, 110B through an input/output opening by aligning the automated transfer mechanism with the tile 161A, 161B, 161C in front of the desired opening. In other aspects, the storage zones 110A, 110B may have any suitable closure(s) for maintaining the samples stored in the trays 370 at any suitable predetermined temperature. As noted before, in other aspects no closures may be provided between the storage and other section.

Figure 1E:
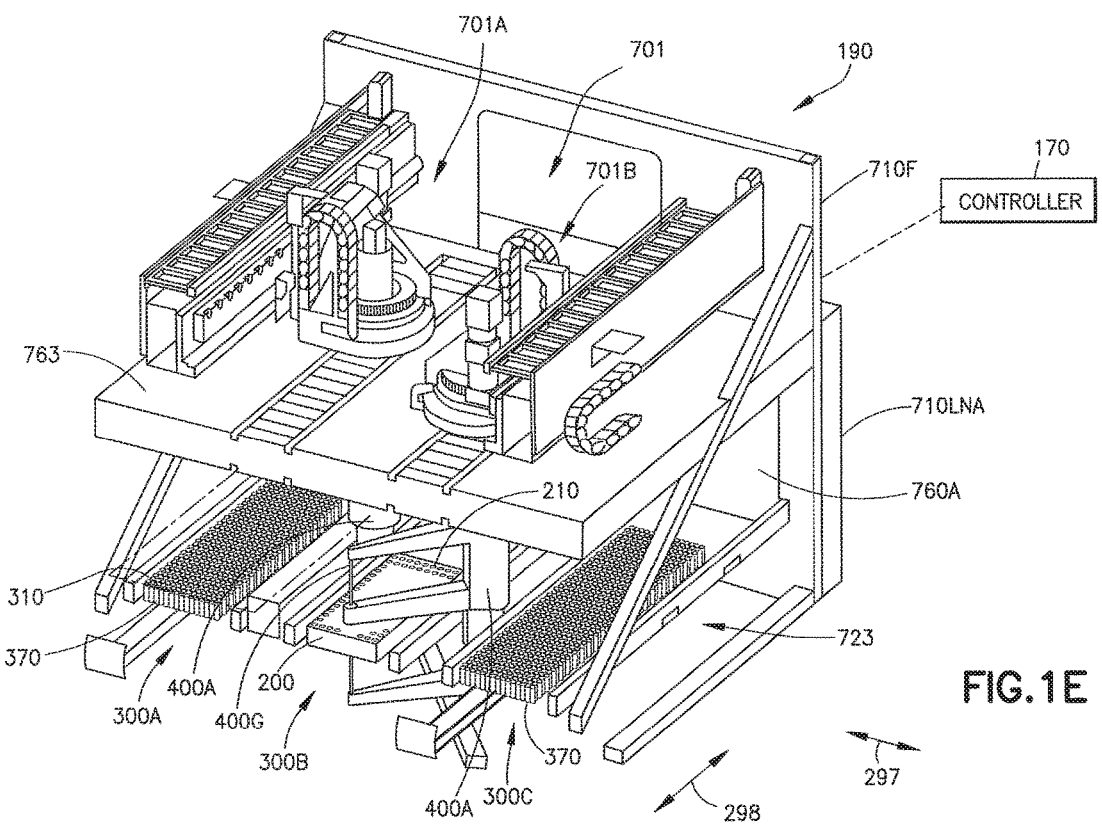
FIG. 1E is a schematic illustration of a portion of a sample selector module in accordance with aspects of the disclosed embodiment.
Figure 1F:
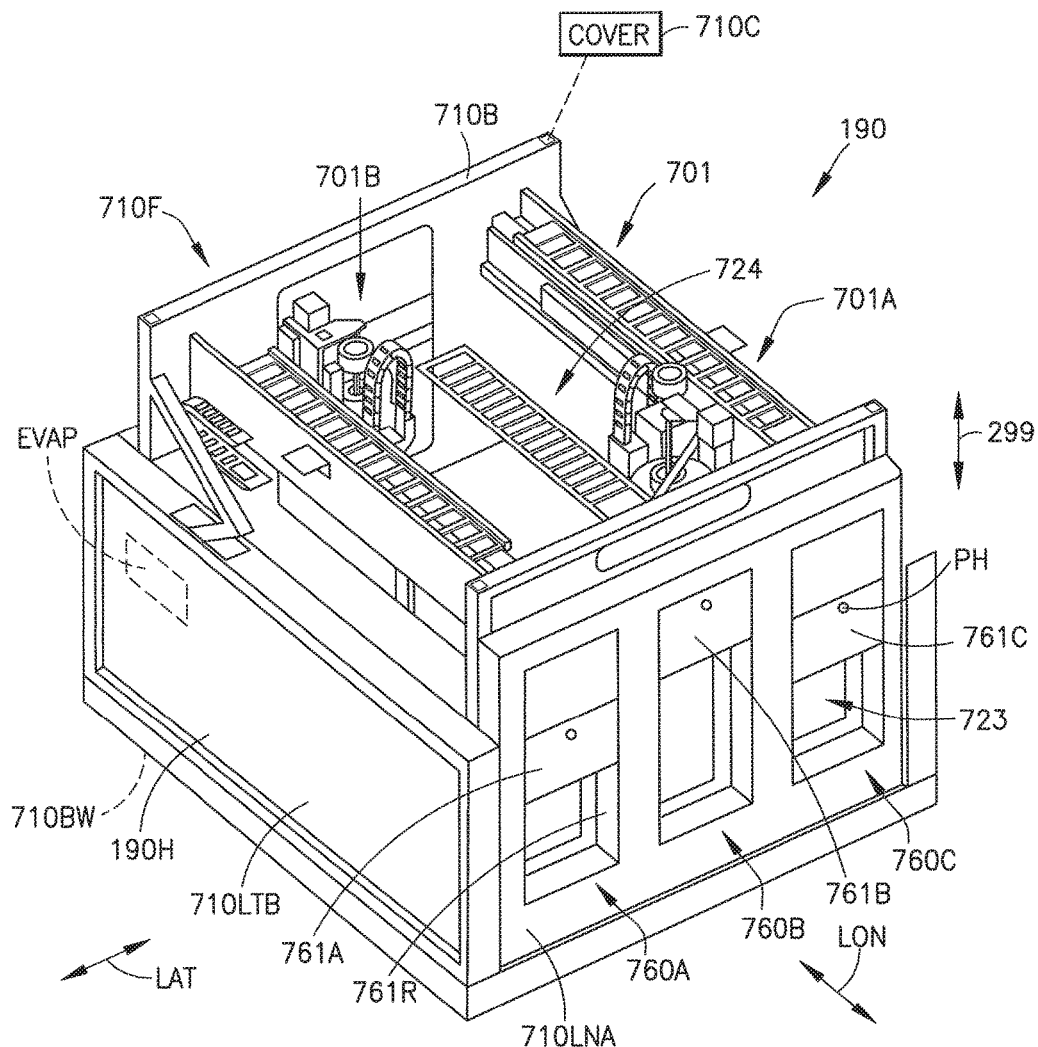
FIG. 1F is a schematic illustration of a portion of the sample selector module of FIG. 1F in accordance with aspects of the disclosed embodiment.
Figure 1G:
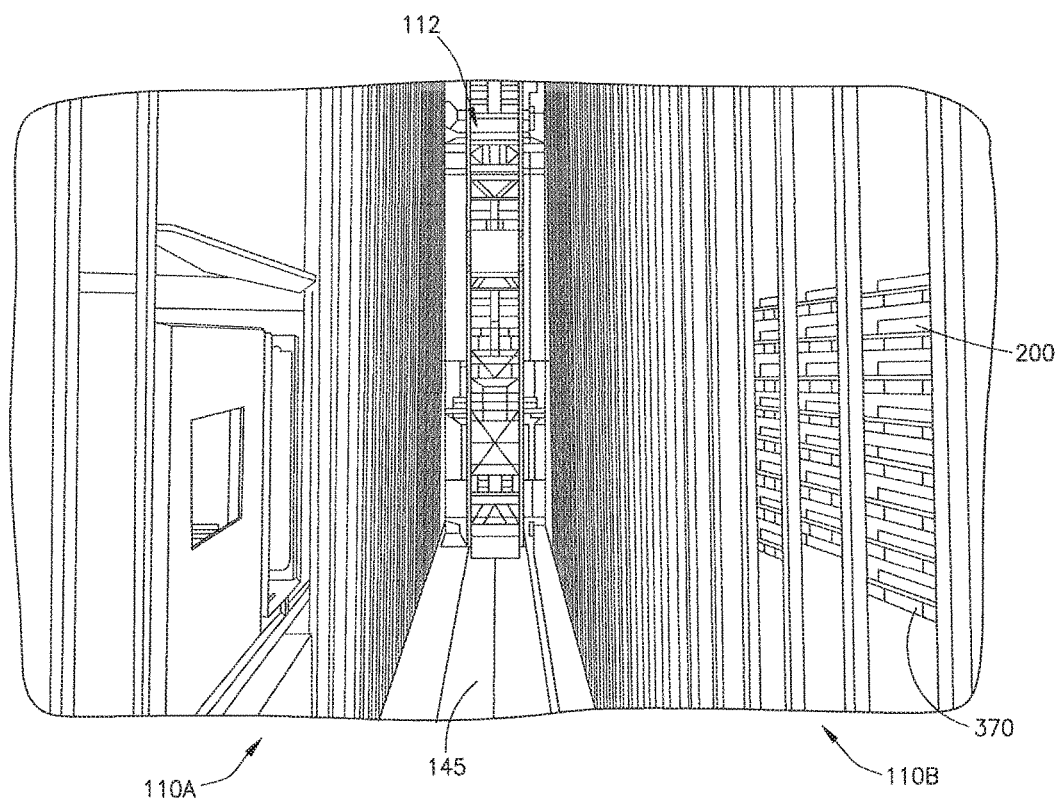
FIG. 1G is a schematic illustration of a portion of a sample storage facility accordance with aspects of the disclosed embodiment
Figure 1H:
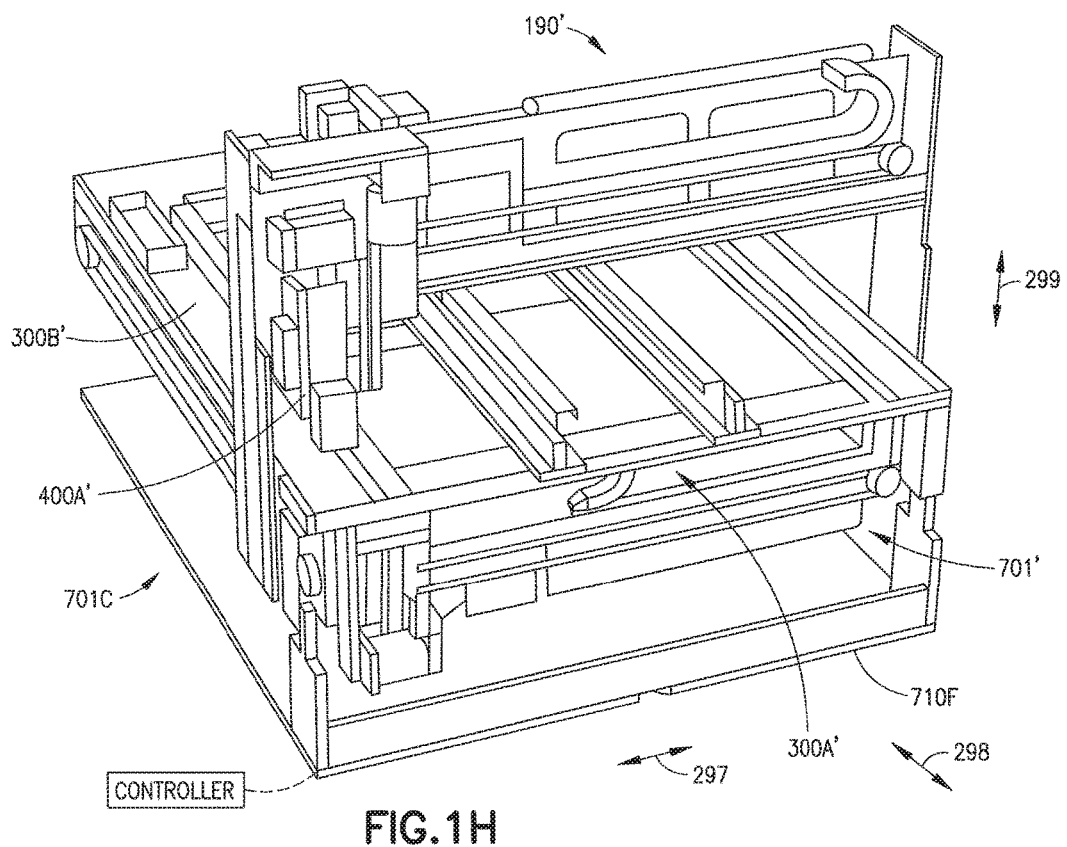
FIG. 1H is a schematic illustration of a portion of a sample selector module in accordance with aspects of the disclosed embodiment.

Referring now to FIGS. 1E, 1F and 1H, the transport shuttle 112 (a representative configuration is shown for example purposes) may be configured to transport the sample trays 370 and/or the sample trays 200 between the storage zones 110A, 110B and any other components of the sample storage facility, which may include but is not limited to transport of sample trays 370 and/or sample trays 200 to and from the sample selector modules 190, 190'. In one aspect, each sample selector module 190, 190' has a representative configuration that provides an isolated or sealed environment for sample selection, and includes a frame 710F, at least one transfer device or unit 701A, 701B, 701C having a drive section 701, 701' connected to the frame 710F and at least one transfer arm portion 400A, 400A' movably connected to the drive section 701, 701'. The frame 710F may include a cover portion 710C and a base portion 710B or include any suitable number of panels/walls (or a unitary/one piece panel) that form/forms a housing 190H configured to hold at least one isolated or sealed environment therein. In one aspect, the housing 190H may include a longitudinal axis LON and a lateral axis LAT and may be divided into other zones/areas. In one aspect the base portion 710B includes lateral walls 710LTA, 710LTB, longitudinal walls 710LNA, 710LNB, a bottom wall 710BW and an isolation member 763 disposed opposite to and spaced apart from the bottom wall 710BW (the term "bottom" is used herein for exemplary purposes only and in other aspects any suitable spatial identifiers may be associated with the wall 710BW) so as to form an isolated climate controlled chamber or zone 723. In one aspect the isolated climate controlled chamber 723 may be maintained at any suitable temperature such as those described herein. In one aspect the isolated climate controlled chamber 723 may be actively cooled while in other aspects the isolated climate controlled chamber 723 may be cooled in any suitable manner. One or more evaporators EVAP may be disposed within the isolated climate controlled chamber 723 and be configured to maintain, for example, a uniform temperature distribution within the isolated climate controlled chamber 723. In one aspect the one or more evaporators may be disposed on a surface of the isolation member 763 forming an interior wall of the isolated climate controlled chamber 723 (e.g. on a ceiling of the chamber). In other aspects the one or more evaporators EVAP may be disposed at any suitable location within the isolated climate controlled chamber 723An isolation member 763 may also be disposed (see FIG. 1C) so as to form a drive section chamber 724 that may be maintained at any suitable predetermined temperature suitable for the operation of drive section 701 components. At least one of the longitudinal walls 710LNA, 710LNB and the lateral walls 710LTA, 710LTB may include one or more input/output openings or apertures 760A 760B, 760C through which sample trays 200, 370 pass for insertion to and removal from the isolated climate controlled zone 723. In another aspect, each sample selector module 190' (as illustrated in the representative example shown in FIG. 1H) may have an open configuration so that the environment therein is common to the storage environment. Similar features are similarly numbered.

As may be realized, the sample trays/microplates 200, 370 are held within the frame 710F of the sample selector modules 190, 190' in any suitable manner so that sample store and transport tubes 250 (referred to herein as sample tubes 250) are transferred between the sample trays 200, 370 by the at least one transfer arm portion 400A as described herein (the at least one transfer arm portion includes a sample tube gripper 400G configured to grip, e.g., the sample tube 250 in any suitable manner such a by the transport gripper interface 253 described herein). In one aspect, high density trays 370 are located in holding locations 300A, 300C on lateral sides of sub-optimal microplate 200 (which is disposed in holding location 300B) so that samples may be transferred between the sub-optimal microplate 200 and both high density trays 370 such as when sample tubes 250 are to be placed sub-optimal microplate 200 for storage and transfer from the sample storage facility 100. In other aspects, sub-optimal microplates 200 may be located in holding locations 300A, 300C while a high density tray 370 is located in holding location 300B so that sample tubes 250 may be transferred between both sub-optimal microplates 200 and the high density tray 370 such as when sample tubes 250 are to be stored within storage zones 110A, 110B. In still other aspects, the sub-optimal microplate and high density trays 370 may be placed in any suitable holding areas of the sample selector modules 190. For example, as illustrated in FIG. 1H the high density trays 370 may be held at location 300A' while the sub-optimal microplates are held in area 300B' adjacent the location 300A'. Further, while in one aspect, three holding locations 300A, 300B, 300C are illustrated, in other aspects, the sample selector modules may have more or less than three holding locations (configured to hold in one aspect, any combination of sub-optimal microplates 200 and high density trays 370 or in other aspects, sub-optimal microplates 200) and a corresponding number of transfer arm portions 400A. Again referring to FIG. 1H in one aspect, the drive section 701' is a gantry drive system that provides the transfer arm portion or pick head 400A' with movement in directions 297, 298, 299.

Each input/output opening(s) 760A, 760B, 760C may be a sealable or otherwise closable opening that is sealed or otherwise closed by a respective sliding tile 761A, 761B, 761C substantially similar to those described above while in other aspects, the input/output opening(s) may be sealed/closable in any suitable manner or may be open (see FIG. 1H).

In one aspect, the antechamber 150 is climate controlled and may include doors 150D1, 150D2 for providing personnel access to the at least the transport zone 145 and/or to the sample selector modules 190, at least part of which may be disposed within the antechamber 150 (e.g. the sample selector modules 190 may be mounted through a wall separating the antechamber 150 from the transport zone 145. As may be realized, the antechamber 150 may be maintained at any suitable temperature allowing fur human entry into the antechamber 150.

The sample storage facility 100 may include any suitable refrigeration system(s) 125 and/or dehumidification system(s) 120 for maintaining respective predetermined temperatures within the different zones of the sample storage facility 100. In one aspect the transport zone 145, transport shuttle 112, tile wall 115, storage zones 110A, 110B, transport zone 145 and input/output modules of the sample storage facility 100 may be substantially similar to those described in U.S. Pat. No. 7,635,246 issued on Dec. 22, 2009, U.S. Pat. No. 7,648,321 issued on Jan. 19, 2010, U.S. Pat. No. 7,793,842 issued on Sep. 14, 2010, U.S. Pat. No. 8,252,232 issued on Aug. 28, 2012 and U.S. patent application Ser. No. 13/595,817 filed on Aug. 27, 2012 and U.S. patent application Ser. No. 13/334,619 filed on Dec. 22, 2011, the disclosure of which are incorporated by reference herein in their entireties.

FIG. 1B illustrates a sample storage facility 100' in accordance with aspects of the disclosed embodiment. The sample storage facility 100' may be substantially similar to sample storage facility 100 described above and include any suitable number of environmental storage zones or areas 110A, 110B, 145 that may be isolated from one another. Here one or more sample selector modules 190 may be mounted through an exterior wall of the sample storage facility 100' rather than through a wall separating/isolating the antechamber 150 from the transport zone 145 or any other suitable zone of the sample storage facility 100.

FIG. 1C is a schematic illustration of sample selector modules 190 (in other aspects sample selector module 190' may be similarly arranged). As may be realized, any suitable number of sample selector modules (two are shown in FIG. 1C) may be stacked one above the other as shown in FIGS. 1B and 1C or disposed side by side as illustrated in FIG. 1A. Each sample selector module 190 may be connected to or otherwise include any suitable refrigeration or climate control system 190R configured to maintain at least a portion of an interior (formed by housing 190H) of the sample selector 190 at a predetermined temperature such as those described herein or in other aspects as described in, for example, U.S. patent application Ser. No. 14/229,077 filed Mar. 28, 2014 (previously incorporated by reference). In one aspect each sample selector module 190 may have a respective climate control system 190R while in other aspects a common climate control system may be provided for two or more sample selector modules 190 or the sample selector module(s) may share a common climate control system with other components (such as storage zones 110A, 110B) of the sample storage facility 100, 100'. In other aspect, no refrigeration or climate control system may be provided.

Referring also to FIG. 1D one or more sample selector modules 190, 190' (and, in some instances, the respective refrigeration system 190R) may be mounted to, for example, the transport shuttle 112 so that the one or more sample selectors 190, 190' move as a unit with transport shuttle 112. Here the transport shuttle 112 may include a transfer arm 112A configured to remove sample trays from the storage zones 110A, 110B (or any other suitable location of the sample storage facility 100, 100') and place sample trays 370 within the one or more sample selector modules 190 disposed on the transport shuttle 112. One or more samples from the sample trays 370 may be sorted and/or transferred to a different tray, such as between source and destination trays, within the sample selector module 190, 190' allowing the source tray to placed back into the storage zone 110A, 110B. In one aspect the source and/or destination tray may be the sub-optimal microplate 200. As may be realized, in aspects where the sample storage zone is the same temperature in which the transport shuttle 112 operates the sample selector 190, 190' may not have a temperature controlled environment but may be open to the transport shuttle operating environment.

Any suitable controller 170 may be connected to the sample storage facility 100, 100' in any suitable manner, such as through a wired or wireless connection. The controller 170 may be configured to control the operation of the sample storage facility 100, 100' in the manner described herein. For example, the controller 170 may include any suitable memory and processors and be configured to track which samples are inserted and/or removed from the sample storage facility 100, 100' and a location of each sample within the sample storage facility 100, 100'. The controller 170 may also be configured to control automation within the sample storage facility where the automation includes, but is not limited to, the transport shuttle 112 and sample selector modules 190 to transfer samples as described herein. In one aspect, the controller 170 is configured to effect storage of the sample store and transport tubes 250 within the high density sample storage tray 370 in an efficient/optimized distribution for the capacity of the high density sample storage tray 370.

Figure 2A:
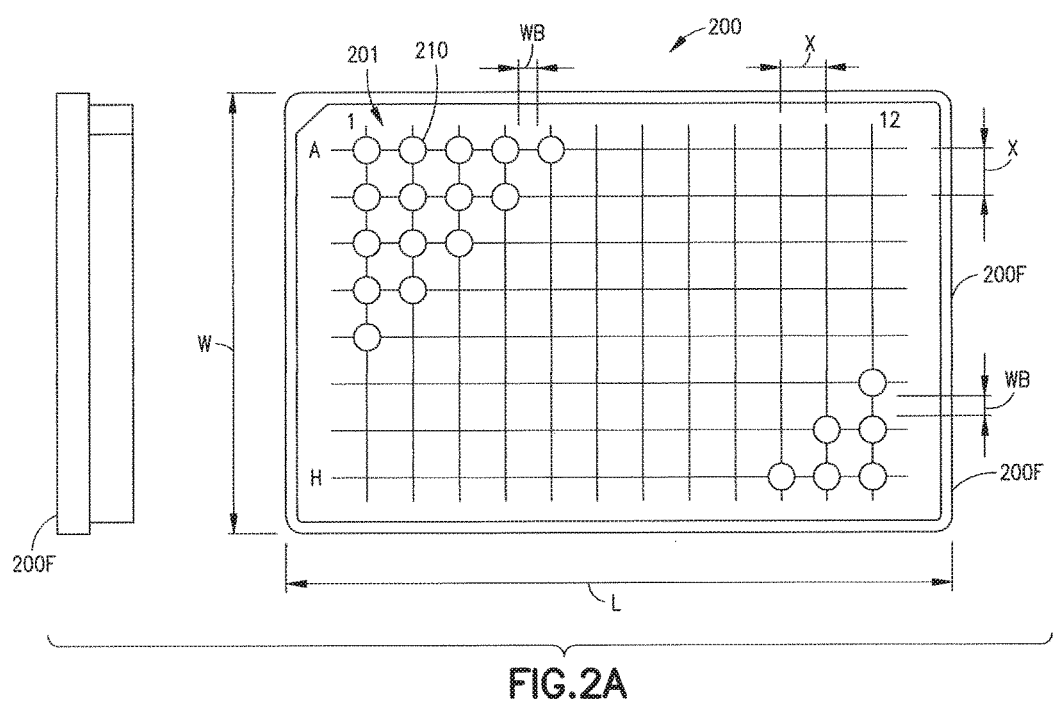
FIG. 2A is a schematic illustration of a sub-optimal microplate in accordance with aspects of the disclosed embodiment.
Figure 2B:
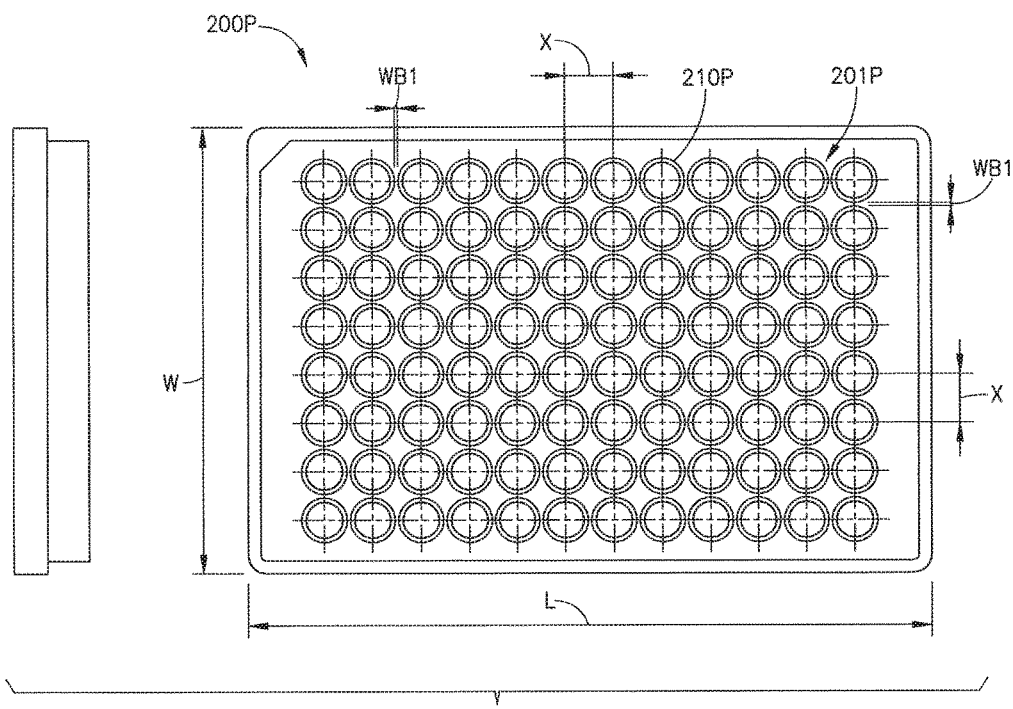
FIG. 2B is a schematic illustration of a prior art microplate.
Figure 2C:
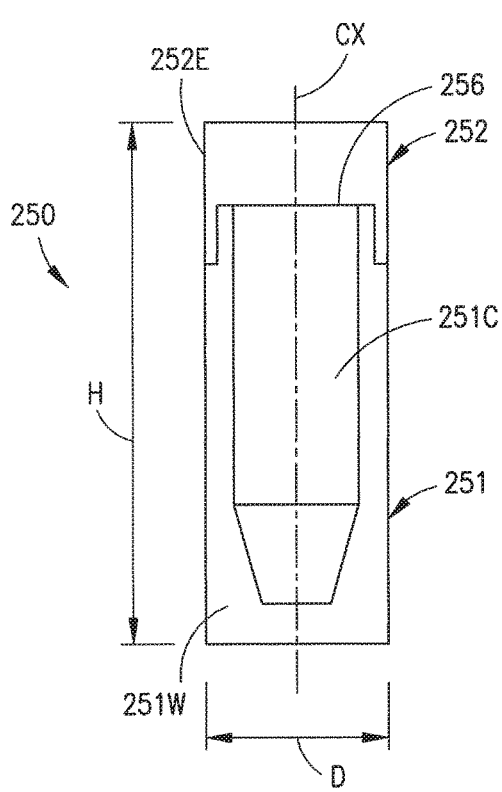
FIG. 2C is a schematic illustration of a sample store and transport tube in accordance with aspects of the disclosed embodiment.
Figure 2D:
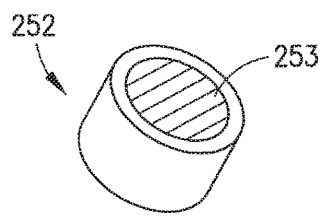
FIGS. 2D-2F are schematic illustrations of portions of the sample store and transport tube of FIG. 2C in accordance with aspects of the disclosed embodiment.
Figure 2E:
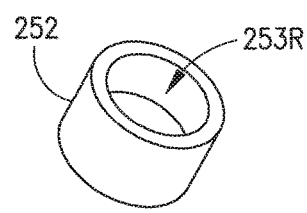
Figure 2F:
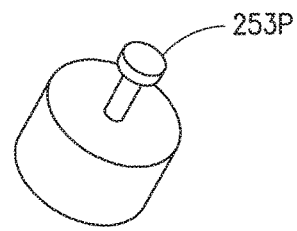
Figure 3:
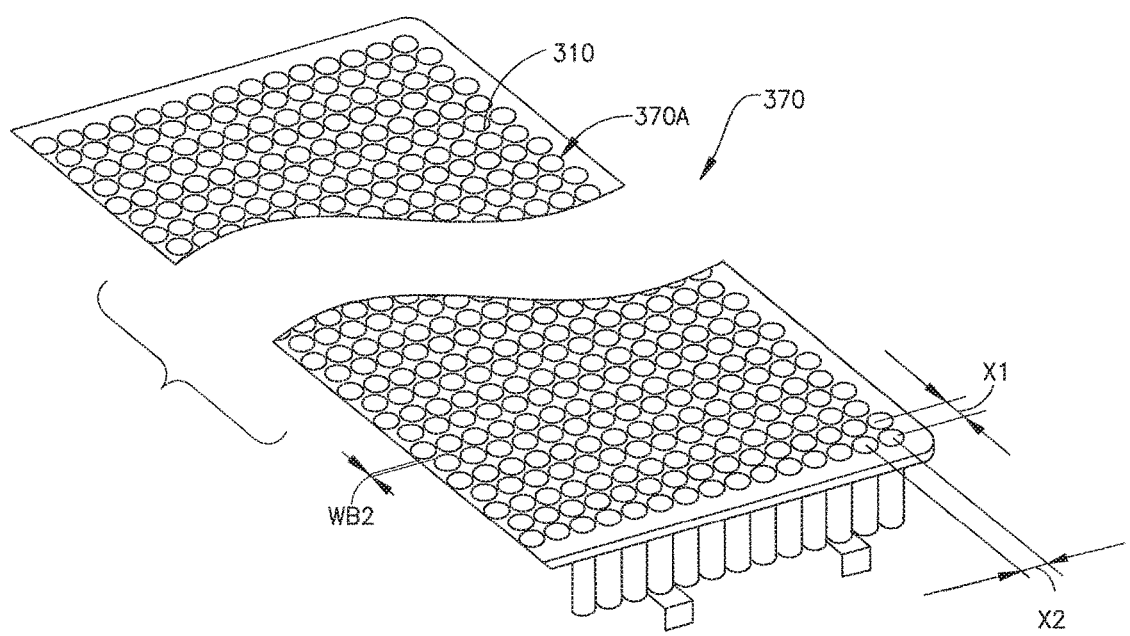
FIG. 3 is a schematic illustration of a high density sample storage tray in accordance with aspects of the disclosed embodiment.
Figure 7:
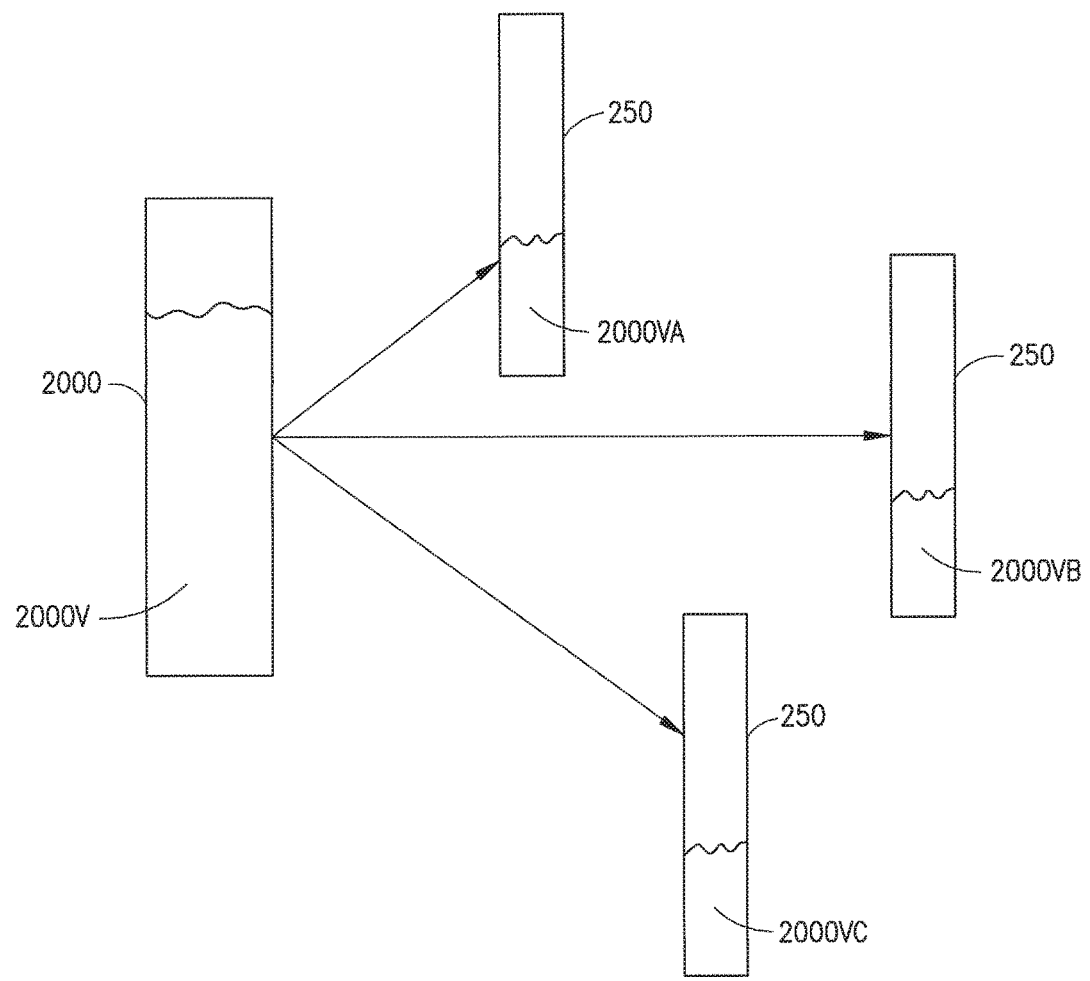
FIG. 7 is a schematic illustration of sample distribution in accordance with aspects of the disclosed embodiment.

Referring to FIGS. 2A, 2C and 3, in accordance with aspects of the disclosed embodiment, the sample storage facility 100, 100' is configured to store and transport sample tubes 250 that are smaller than conventional 9 mm sample tubes 2000 (see FIG. 7 having diameters of under 9 mm, i.e. the pitch between sample holding areas or receptacles of the standard format SBS sample tray. In accordance with aspects of the disclosed embodiment each of the sample tuber 250 have a sample holder 251 and a cap 252 which may be constructed of any suitable materials. In one aspect the cap 252 may be constructed of any suitable plastic, glass filled plastic composite, rubber or any other suitable material. The sample holder 251 may include at least one peripheral wall 251W extending longitudinally along a central or longitudinal axis CX where the at least one peripheral wall 251W forms an opening 256 and a cavity 251C communicably connected to the opening 256. The at least one peripheral wall 251W may close the cavity 251C at one end of the sample holder 251 so that the cavity 251C holds sample(s) therein. As may be realized, the sample holder 251 may have any suitable shape such as a cylindrical or test tube configuration but in other aspects the sample holder 251 may have any suitable configuration with any suitable number of peripheral walls. The cap 252 may have any suitable configuration for engaging the sample holder 251 and closing the opening 256. In one aspect, the cap 252 may have a cylindrical body having at least one peripheral wall forming an outer peripheral edge or side 252E of the cap 252 and defining the bounds within which the cap 252 (and hence the sample tube 250) is gripped by, for example, one or more of the shuttle 112 and sample selector modules. In one aspect the cap 252 and or sample holder 251 may be substantially similar to that described in U.S. application Ser. No. 14/671, 423 filed on Mar. 27, 2015, the disclosure of which is incorporated herein by reference in its entirety. For example, referring also to FIGS. 2D-2F, the cap 252 may have a transport gripper interface 253 that may form a recess 253R in the cap 252 as shown in FIG. 2E. Where the recess 253R is provided the grippers/transport of the transport shuttle 112 and/or sample selector modules 190 may be configured for insertion into the recess 253R for gripping the cap 252 (and hence the sample tube 250) where the gripping force is a radially outward gripping force. In other aspects, the transport gripper interface 253 may form a protrusion 253P as illustrated in FIG. 2F where the grippers/transport of the transport shuttle 112 and sample selector modules 190 may be configured for gripping the cap 252 (and hence the sample tube 250) by the protrusion 253P where the gripping force a radially inward gripping force. In other aspects, the gripper interface 253 may include a magnetic interface that is configured to interface with magnetic gripper of the transport shuttle 112 and sample selector modules 190. In still other aspects, the transport gripper interface 253 may be any suitable interface configured for interfacing with the grippers of the transport shuttle 112 and sample selector modules 190.

As described herein, the standard format SBS microplate is specified in ANSI SLAS 4-2004 (R2012) (formerly recognized as ANSI/SBS 4-2004) and ANSI SLAS 1-2004 (R2012) (formerly recognized as ANSI/SBS 1-2004), both previously incorporated by reference herein in their entireties. As described herein, the sub-optimal microplates 200, in which the sample tube(s) 250 are held/stored, are configured to conform to the standard SBS sample tray footprint and pitch as described in greater detail below. The sub-optimal microplates 200 may also have a center to center distance or pitch X between sample tube holding areas or receptacles 210 of about 9 mm, which is the standard center to center pitch for a standard 96 well SBS microplate or tray. However, while the sub-optimal microplates 200 have a standard SBS footprint and a standard SBS center to center sample tube holding area pitch X, the configuration of tube holding receptacles 210 of the array 201 of the sub-optimal microplate 200 is a suboptimal density with respect to a density of a microplate with an SBS standard footprint dimension and holding receptacle to web wall thickness ratio for optimum array volume capacity (such as the standard SBS tray holding 9 mm tubes). For example, the sub-optimal microplates 200 have sub-optimal sample tube holding areas receptacles 210 that provide for a sub-optimal volume array, as noted above, when compared to the storage of conventional 9 mm sample tubes that effects an optimized sample density, at least in the storage area, and storage racks 370 and per predetermined length of the store and transport axis (e.g. the sub-optimal volume array of the sub-optimal microplate 200 is optimized for sample density). For example, in accordance with the aspects of the disclosed embodiment, the web walls WB between sample tube holding areas or receptacles 210 of the sub-optimal microplates 200 have an increased thickness (as described in greater detail below) compared to the web walls WB1 (see FIG. 2B) between the sample tube holding areas or receptacles 210P of the standard SBS microplate 200P such that the footprint (e.g. the length L and width W) and pitch X of the sub-optimal (volume) microplate 200 are decoupled from a diameter of the sample tubes 250 (and hence a diameter of the tube holding receptacles 210). As may be realized, the size and shape of the tube holding receptacles 210, in accordance with the aspects of the disclosed embodiment, are sub-optimal (volumetrically) when compared to the size and shape of the tube holding receptacles 210P of a conventional 96 well SBS microplate having tube holding receptacles 210P configured to hold about a 9 mm diameter sample tube. In one aspect, the cap 252 and sample holder 251 of the sample tube 250 each have a diameter D substantially less than the about 9 mm pitch between, for example, the sample tube holding areas or receptacles of a standard format 96 well SBS microplate or tray. In one aspect, the sample tubes 250 may have any suitable geometry such as, for example, having a round cross-section, a square cross-section or a combination of round and square cross-sections (e.g. in the same tube). In one aspect, the sample tube 250 has an outside diameter D of about 6.0 mm (referred to herein as a 6 mm tube) with a tube working volume of about 0.1 ml, while in other aspects, the diameter D of the sample tube 250 may be more or less than about 6.0 mm (e.g. such as about 5.8 mm) with a working volume of more or less than about 0.1 ml. In one aspect the sample tube 250 may have any suitable height H. In one aspect, the sample tube 250 may be elongated so as to have a capacity of about 0.26 ml. In one aspect, the narrow diameter tubes, in combination with the sub-optimal or under volume microplates 200 and high density storage trays/racks 370, provide increased throughput by providing an increased number of available tubes to the picker for a predetermined length or area of storage space of the store and selector module. In one aspect, tubes having a diameter about 6.8 mm in diameter may be held in a sub-optimal volume microplate having a web-thickness WB of about 2.2 mm where in other aspects tubes having a diameter of less than 8 mm may be held in a sub-optimal volume microplate having a web thickness WB of more than 1 mm, as described in greater detail below. As may be realized, the high density trays/racks 370 (FIG. 3) may hold about 1600 6.8 mm diameter tubes and result in about a 1.6 times increase in throughput when compared to an optimized (for volume capacity) tray holding 9 mm diameter tubes. As an example, when the sample tubes 250 are stored in the sub-optimal volume microplate 200 (e.g. having a pitch X of about 9 mm between sample holding areas or receptacles 210) the volume of sample stored in sub-optimal microplate 200 is less than that stored in a standard 96 well SBS microplate with conventional 9 mm sample tubes (e.g. having the same or similar height H as the sample tube 250). For example, a 9 mm sample tube may have an inside diameter of about 6.83 mm while the inside diameter of the tube 250 may be about 3.59 mm (in other aspects the inside diameter may be more or less than about 3.59 mm). As such, the volume of sample stored, for tubes having the same height, a ratio of areas, i.e. 1:3.62 in favor of the conventional sample tube (e.g. the storage density in μl/sample is greater for the conventional 9 mm sample tubes stored in the standard 96 well/receptacle SBS microplate when compared with the storage density in μl/sample for the sample tubes 250 stored in the sub-optimal microplate 200, e.g. having 96 receptacles 210).

However, in the aspects of the disclosed embodiment, when the sample tubes 250 are placed in the storage zones 110A, 110B of the sample storage facility 100, 100' the high density storage trays/racks 370 are not bound by the standard SBS pitch between samples (e.g. for compatibility with conventional sample transport and testing equipment as noted above) such that the sample tubes 250 are stored in high density/capacity (HD) tray configuration. For example, the sample trays 370 include an array 370A of tube/sample holding areas or receptacles 310 that have a capacity related to the under optimum volume capacity of the microplate 200 with an optimized center to center pitch X1, X2 between the sample holding receptacles 310 (e.g. so that a web WB2 thickness between sample holding receptacles 310 is minimized) where the sample trays each hold about 2000 sample tubes 250 (which may be about double the storage capacity of a high density sample tray having the same footprint and that holds conventional 9 mm sample tubes). As may be realized, the smaller sample tubes 250 provide for an increased number of sample tubes 250 for the same storage size (when compared to the storage of the conventional 9 mm sample tubes). This increased number of sample tubes 250 within the storage facility 100, 100' in turn increases the sample placement/count and distribution of samples within the sample storage facility 100, 100'. The increased sample placement/count and distribution of samples results in an increase in the likelihood of "hitting" (e.g. increased sample "hit rate") or picking of a sample tube ordered for a given transport pick/place action of the transport system (e.g. such as a pick/place action of the transport shuttles 112 and/or the sample selector modules 190). For example, increasing the distribution a number of samples on/in a sample tray 370 increases the likelihood that the sample being ordered is within the sample tray 370 from which another sample was previously picked (e.g. in a common tray 370). As may be realized, there are more "copies" of samples placed in storage thereby increasing the likelihood that the ordered sample will be available in a picked sample tray 370. In other aspects, more samples to pick from in a given sample tray 370 also provides for increased picks from a common tray (e.g. less down time for the sample tube 250 picker of the transport shuttle 112 and/or sample selector modules 190) which increases the picking throughput of the sample storage facility 100, 100'. Typical "hit rates" (e.g. the percentage of tubes selected when picking tubes from a tray) are in the range of 0.1% to 2%. At 0.1% the number of tubes to be picked, on average in a tray with around 1000 tubes is 1, at 0.2% two tubes per tray is the average, and so on. As may be realized, the increased number and distribution of samples in the sample tray 370 increases the hit rates of sample tubes 250 picked from a common tray 370 effecting more picks in a given time period from the common sample tray 370. In one aspect, the controller 170 is configures so that the distribution of sample store and transport tubes 250 and the capacity of the high density sample storage tray 370 effects an increased pick rate in sample store and transport tube picking relative to a standard capacity of a high capacity tray and storage area with optimal volume capacity arrayed tube holding receptacles (e.g. for holding the about 9 mm diameter sample tubes). In accordance with the aspects of the disclosed embodiment the storage area with optimal volume capacity arrayed tube holding receptacles is a storage area with a standard SBS pitch between tube holding receptacles that are configured provide optimum sample volume capacity for the storage.

Figure 4A:
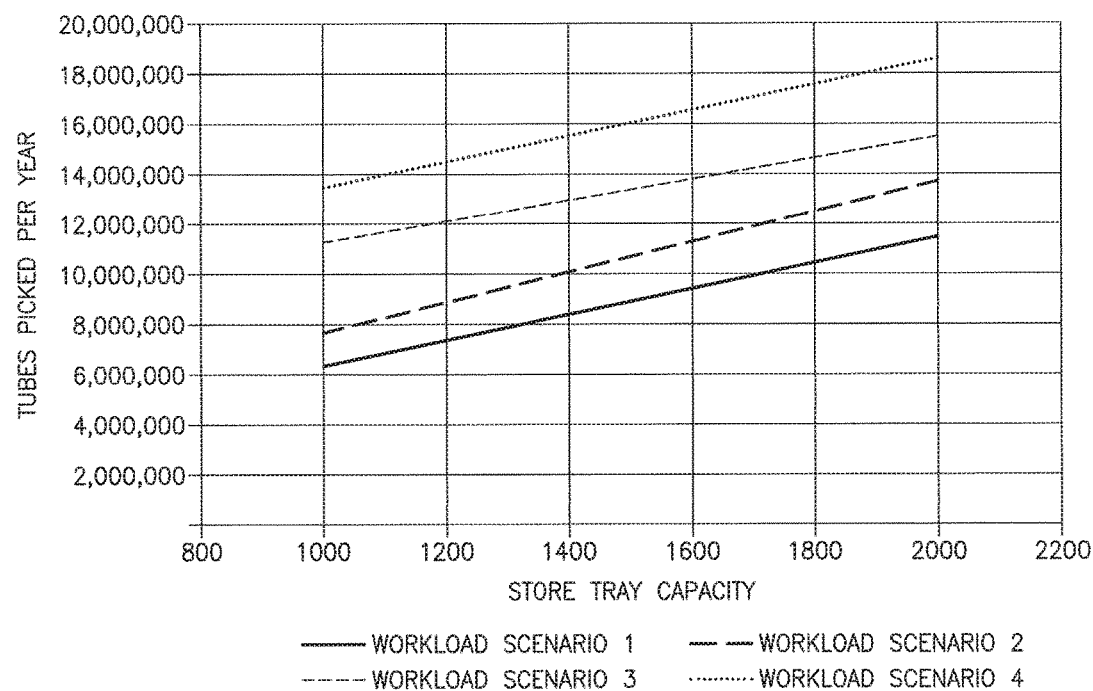
FIGS. 4A and 4B are graphs in accordance with aspects of the disclosed embodiment.
Figure 4B:
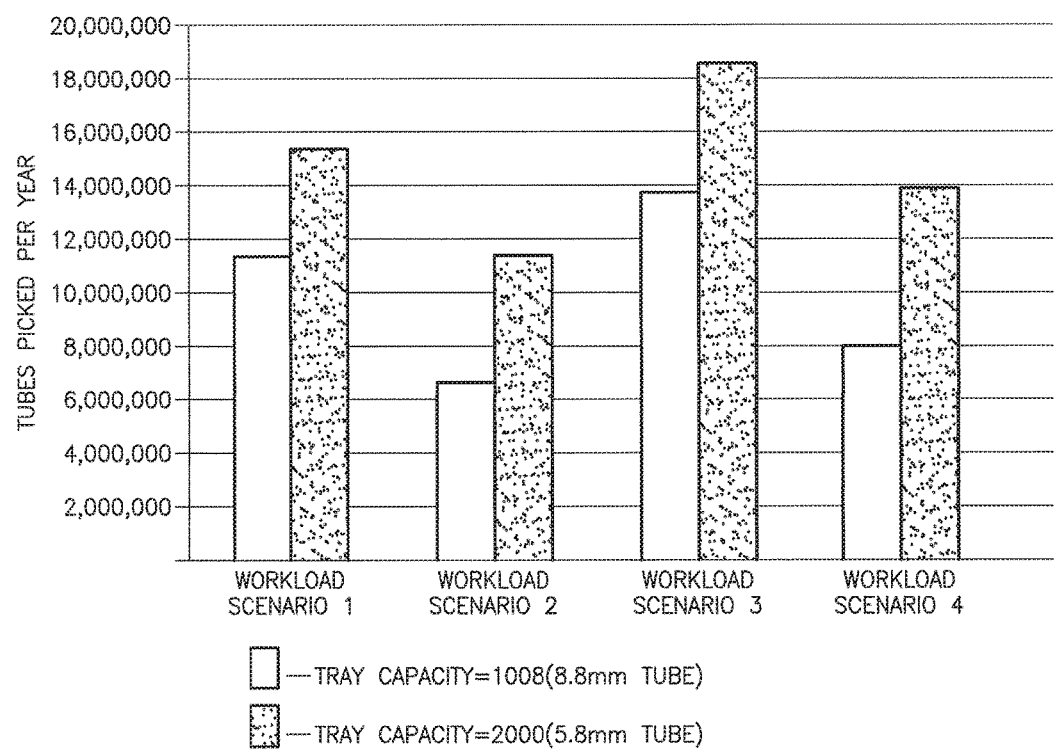

It is noted that modern drug discovery techniques are focusing on assembling many more custom sets of samples which would benefit from increased tube picking throughput (when compared to the picking of conventional 9 mm sample tubes) as provided by the aspects of the disclosed embodiment. Referring to FIGS. 4A and 4B, a graphical illustration of the relationship between sample tube diameter/sample tray capacity and tubes picked per year is provided for four workload scenarios. The graphs in FIGS. 4A and 4B model real ordering scenarios (e.g. multiple orders of different sizes and response time requirements) and the narrow aisle store architecture illustrated in FIGS. 1A and 1B. As can be seen in FIGS. 4A and 4B, the small sample tube 250 (e.g. having a diameter of about 6 mm), in accordance with the aspects of the disclosed embodiment, may provide about a 70 % increase in samples picked over the conventional 9 mm sample tube where about 2000 sample tubes 250 are stored on each sample tray 370 compared to about 1000 conventional 9 mm sample tubes stored on each sample tray.

In addition, as noted above, the sample storage facility 100, 100' also includes a storage array 140 formed by the sub-optimal microplates 200 (as described above a portion of the storage areas/arrays 110A, 110B may also be formed by the sub-optimal microplates 200). In one aspect, the storage array 140 may be formed by one more sub-optimal volume microplate(s) 200 placed or located at a suitable location or station (stationary or movable) in the storage facility 100, 100', such as for buffering or placement in connection with sample loading and unloading from the storage facility 100, 100'. Storage array 140 may also define an intermediate storage area in the storage facility 100, 100' in connection with outer suitable intra-facility sample transport or transfer. In one aspect, the storage array 140 is separate and distinct from the storage zones 110A, 110B of the sample storage facility 100, 100', e.g. a buffer or placement location for inter-facility transport. In one aspect, sample tube holding receptacles or areas 210 of the microplate(s) 200 define the storage array 140 for the sample tubes 250 within the sample storage facility 100, 100'. As also noted above, the sub-optimal (volume) microplates 200 are configured to conform to a standard SBS sample tray footprint and pitch as described in ANSI SLAS 4-2004 (R2012) (formerly recognized as ANSI/SBS 4-2004) and ANSI SLAS 1-2004 (R2012) (formerly recognized as ANSI/ SBS 1-2004), both previously incorporated by reference herein in their entireties. For example, the sub-optimal microplates 200 may have a length L of about 127.76 mm and a width of about 85.48 mm. The sub-optimal microplates 200 may also have a center to center distance or pitch X between sample tube holding areas or receptacles 210 of about 9 mm, which is the standard center to center pitch for a standard 96 well SBS microplate or tray. However, while the sub-optimal microplates 200 have a standard SBS footprint and a standard SBS center to center sample tube holding area pitch X, the sub-optimal microplates 200 have sub-optimal sample tube holding areas or receptacles 210 that provide for a sub-optimal volume density, as noted above, when compared to the storage of conventional 9 mm sample tubes that effects an optimized sample density, at least in the storage area, and storage racks 370 and per predetermined length of the store and transport axis (e.g. the sub-optimal volume array of the sub-optimal microplate 200 is optimized for sample density. For example, in accordance with the aspects of the disclosed embodiment, the web walls WB between sample tube holding areas or receptacles 210 of the sub-optimal microplates 200 have an increased thickness compared to the web walls WB1. (see FIG. 2B) between the sample tube holding areas or receptacles 210P of the standard SBS microplate 200P (see ANSI SLAS 4-2004 (2012) and ANSI SLAS 1-2004 (R2012) noted above) such that the footprint (e.g. the length. L and width W) and pitch X of the sub-optimal microplate 200 are decoupled from a diameter D of the sample tubes 250 (and hence a diameter of the tube holding receptacles 210). In one aspect, the sub-optimal microplate may have a pitch X between about 8 mm to about 10 mm and a web wall thickness WB of at least greater than about 1 mm and in one aspect, greater than about 1 mm to about 3 mm. In one aspect, the sample tube holding receptacles or areas 210 of the microplate(s) 200 have a pitch X between the centers of the receptacles 210 and a web wall thickness WB between receptacles 210 where the web wall thickness is at least greater than about 10% of the pitch X. In other aspects the web wall thickness WB is at least about 20% of the pitch X while in still other aspects the web wall thickness WB is greater than about 10% to about 25% of the pitch X. Further, while 96 well microplate(s) are described herein it should be understood that the aspects of the disclosed embodiment are applicable to other storage rack capacities such as for example 384 well tube racks. For example the 384 well tube racks have an SBS standard pitch of about 4.5 mm and the tubes are generally a bit smaller than the pitch. In some aspects, the tubes for the 384 well microplate can have a diameter of about 3 mm to about 4 mm and the web wall thickness of the 384 way microplate would be at least about 0.5 mm and in one aspect about 0.5 mm to about 1.5 mm. In some instances the web wall thickness of the 384 well microplate is at least greater than about 10% of the pitch. In other aspects the web wall thickness of the 384 well microplate is at least about 20% of the pitch while in still other aspects the web wall thickness is greater than about 10% to about 25% of the pitch. It is noted that the optimal microplate as shown in FIG. 2B has a web wall thickness WB1 that is less than 10% of the pitch. In one aspect, the above pitch to web wall thickness also apply to the about 6.8 mm diameter and about 8 mm diameter tubes described above. As noted above, the size and shape of the tube holding receptacles 210, in accordance with the aspects of the disclosed embodiment, are sub-optimal when compared to the size and shape of the tube holding receptacles 210P of a conventional 96 well SBS microplate having tube holding receptacles 210P configured to hold about a 9 mm diameter sample tube.

In one aspect, each sub-optimal microplate 200 includes a plate frame 200F and a predetermined array 201 of tube holding areas or receptacles 210 formed in the frame 200F. As noted above, the tube holding receptacles 210 of the predetermined array 201 are arranged with a SBS standard pitch X that corresponds to the predetermined array 201. Each of the tube holding receptacles 210 of the predetermined array 201 has a sub-optimal size and shape that is configured to hold a sample tube 250 that is disposed for containing a sample specimen(s) in storage within the storage area 140 of the sample storage facility 100, 100'. In one aspect, the sub-optimal tube holding receptacles 210 are shaped to engage the walls 251W of the sample tube 250 to hold the sample tube 250 within the frame 200F where the tube holding receptacles 210 of the predetermined array 201 are arranged so that the sample volume capacity defined by the predetermined array 201 is an under optimum volume capacity. In one aspect, the sub-optimal tube holding receptacles 210 are shaped to conformally engage the walls 251W of the sample tube 250 to hold the sample tube 250 within the frame 200F. For example, the volume of sample held in the array 201 of sample tubes 250 in the sub-optimal microplate 200 is less than a volume of sample held in the array 201P (see FIG. 2B) of a standard 96 well SBS microplate with conventional 9 mm sample tubes. In one aspect, the configuration of the tube holding receptacles 210 in the predetermined array 201 provides for a sub-optimal density with respect to a standard SBS microplate 200P having a standard SBS pitch X. For example, as noted above the thickness of the webs WB between tube holding receptacles 210 is increased compared to a standard 96 well SBS microplate 200P that is optimized to hold conventional 9 mm sample tubes where the standard SBS microplate 200P is optimized with an array 201P of tube holding receptacles 210P that minimizes the web WR1 thickness between the tube holding receptacles 210P and maximizes a size of the tube holding receptacles 210P (e.g. to hold 9 mm sample tubes). As may be realized, because the webs WB between the tube holding receptacles 210 is increased, the size of the sample tubes 250 held by the tube holding receptacles 210 are also sub-optimal. As may be realized, and contrary to the aspects of the disclosed embodiment, the sample tray footprint (e.g. length L and width W), pitch X between sample holding receptacles 210P and the sample tube size are closely related/coupled for the standard format 96 well SBS microplate 200P optimized for holding a 9 mm sample tube.

In accordance with aspects of the disclosed embodiment, the microplates 200 form both the storage area 140 (and/or at least a portion of storage areas 110A, 110B) within the sample storage facility 100, 100' and a transport carriage for sample tubes 250 outside of the sample storage facility 100, 100', such as for transport of the sample tubes 250 to a sample processing/preparation module (e.g. workstation) 163 or any other suitable location of a laboratory, including, but not limited to, reaction preparation modules, multi-tip pipettes stations, automate cap removal and replacement stations, code reading stations (e.g. to read 2-D codes on the sample tubes 250), tube sealing stations, and tube piercing stations. In one aspect the sample tubes 250 are configured for interfacing with an acoustic dispenser or any other suitable dispenser disposed at the sample processing/preparation modules. For example, as noted above, the sample storage facility 100, 100' includes an automated storage and retrieval system that, in one aspect, includes the transport shuttles 112 and/or the sample selector modules 190. In one aspect, the sample selector modules 190 pick one or more sample tubes 250 from the high density storage trays 370 and transfer the one or more sample tubes 250 to the microplate 200 for placement and storage in the storage area 140 formed by the microplates 200. In other aspects, the sample selector modules 190 pick one or more sample tubes 250 from the microplate 200 and transfer the one or more sample tubes 250 to the high density storage trays 370 for placement and storage in the storage zones 110A, 110B. In one aspect, the storage area or array 140 within the sample storage facility 100, 100' is formed by (e.g. defined by) the predetermined array 201 of tube holding receptacles 210 of the microplates 200. As described herein, the automated storage and retrieval system is configured for the automated storage and retrieval of sample store and transport tubes from the sample storage zones 110A, 100B with a predetermined throughput capacity to the storage array 140. In one aspect, the storage array 140 is balanced with the predetermined throughput capacity of the automated storage and retrieval system (or at least a portion thereof) so that the sub-optimal density of the tube holding receptacles 250 of the predetermined array 201 effects increased throughput of sample store and transport tubes 250 from the sample storage zones 110A, 110B to the storage array 140 relative to a storage area (similar to storage zones 110A, 110B but configured to hold 9 mm sample tubes) with optimal volume capacity arrayed sample tube receptacles (similar to tube holding receptacles 310 such as in the high density trays 370). In one aspect, the storage array 140 and the automated storage and retrieval system are balanced so that the sub-optimal density of the tube holding receptacles 250 of the predetermined array 201 effects increased throughput of sample store and transport tubes from the sample storage zones 110A, 110B to the storage array 140 for a predetermined transfer action of the automated storage and retrieval system to the storage array, relative to the storage area with optimal volume capacity arrayed tube holding receptacles.

In one aspect, the sub-optimal density of the tube holding receptacles 250 of the predetermined array 201 of the microplate(s) 200 is matched or balanced with the characteristics of the sample storage facility 100, 100' automated storage and retrieval system or at least a portion thereof, where the automated storage and retrieval system includes the shuttle 112 and/or sample selector modules 190. For example, a sample tube 250 distribution in the sample storage facility 100, 100', such as in the sample tube holding receptacles 210 of the microplates 200 (and/or high density trays 370) is optimized for throughput. In one aspect, the tube distribution and placement in the sample storage zones 110A, 110B are balanced with the storage array 140 so that the sample storage zones 110A, 110B have a sample store and transport tube capacity that effects increased throughput of sample store and transport tubes from the sample storage zones 110A, 110B to the storage array 140 relative to the storage area with optimal volume capacity arrayed tube holding receptacles. In one aspect, the storage capacity of the high density trays 370 is doubled (e.g. about 2000 sample tubes 250 per tray 370 compared to trays holding conventional 9 mm sample tubes) where the sample tubes 250 are arranged within the high density trays 370 in an efficient/optimized distribution. The efficient/optimized distribution may be any suitable distribution such as, for exemplary purposes, a pseudo random distribution, a rules based weighted distribution or any other distribution that results in a maximum probability of finding a predetermined sample tube 250 within a predetermined high capacity tray

370. Here the increased storage density and/or the efficient distribution of the sample tubes 250 effects optimization of the hit rate for a given storage space and transport motion (e.g. such as a pick place motion of the sample selector modules 190 from the high density trays 370 to the microplates 200). In one aspect, referring again to FIGS. 4A and 4B, doubling of the high density tray 370 capacity and/or efficient distribution provides about twice the efficiency in picks and about twice the throughput of the automated storage and retrieval system when compared to storage system using, for example 9 mm sample tubes. For example, as illustrated in FIGS. 4A and 4B, the number of tubes picked in systems using 9 mm sample tubes may be represented by a storage tray capacity of about 1000 sample tubes per tray while the sample storage facility 100, 100' in accordance with the aspects of the disclosed embodiment are represented by a storage tray capacity of about 2000 sample tubes 250 per tray 370. As noted above, aspects of the disclosed embodiment may provide about a 70% increase in samples picked over the conventional 9 mm sample tube where about 2000 sample tubes 250 are stored on each sample tray 370 compared to about 1000 conventional 9 mm sample tubes stored on each sample tray as illustrated in FIGS. 4A and 4B.

In one aspect, the efficient distribution optimization of the sample tubes 370 may be provided by any suitable controller 170 connected to the sample storage facility 100, 100'. In one aspect, the efficient distribution optimization may employ any suitable rules based weighting or biasing algorithm configured to place the sample tubes 250 in associated positions within the trays 370. In one aspect, the associated positions may be related to a predetermined characteristic of the sample tubes 250 such as a frequency of tests performed on the samples held in the sample tubes 250, a type of test performed on the samples held in the sample tubes 250, the type of samples held in the sample tubes 250, an interrelationship of the samples/specimens within the sample tubes 250 or any other suitable criteria. For example, in one aspect, the criteria include orders for output can be grouped together using common trays 370, while in other aspects the criteria may include trays located in the sample storage system 100 that will provide the best delivery time to the picker. In still other aspects, the samples may be organized in storage so that samples likely to be picked together are stored together in a common tray. In some aspects controller 170' may direct reorganization of samples in storage, for example, during input/output downtime, so that samples likely to be picked together are stored together on a common tray. In some instances, the controller may use historical picking data to predict future sample picking and to determine and effect efficient organization of samples on trays in storage. In other aspects, the controller 170 may be configured to look ahead in the sample picking sequence on large orders and pick the trays corresponding to the samples in any suitable order so that tray access is more efficient.

Once the sample tubes 250 are located in the microplates 200 the sample tubes 250 are removed from the storage 140 through, for example, input/output modules 130 and transferred to, for example the sample processing/preparation module 163 (or any other suitable location within, e.g., a laboratory such as those described herein) without any further handoff of the sample tubes 250 from the microplate 200 (e.g. the sample tubes 250 remain within the microplate 200 during ingress and egress from the sample store facility 100, 100'). As such, the sub-optimal array 201 density (e.g. the under optimum volume capacity) of the microplate 200 provides for or otherwise forms the transport carriage that is input/output to/from the sample storage facility 100, 100' and transferred between the sample storage area 140 within the sample storage facility 100, 100' and any suitable sample processing module, such as the sample processing/preparation module 163.

Figure 5:
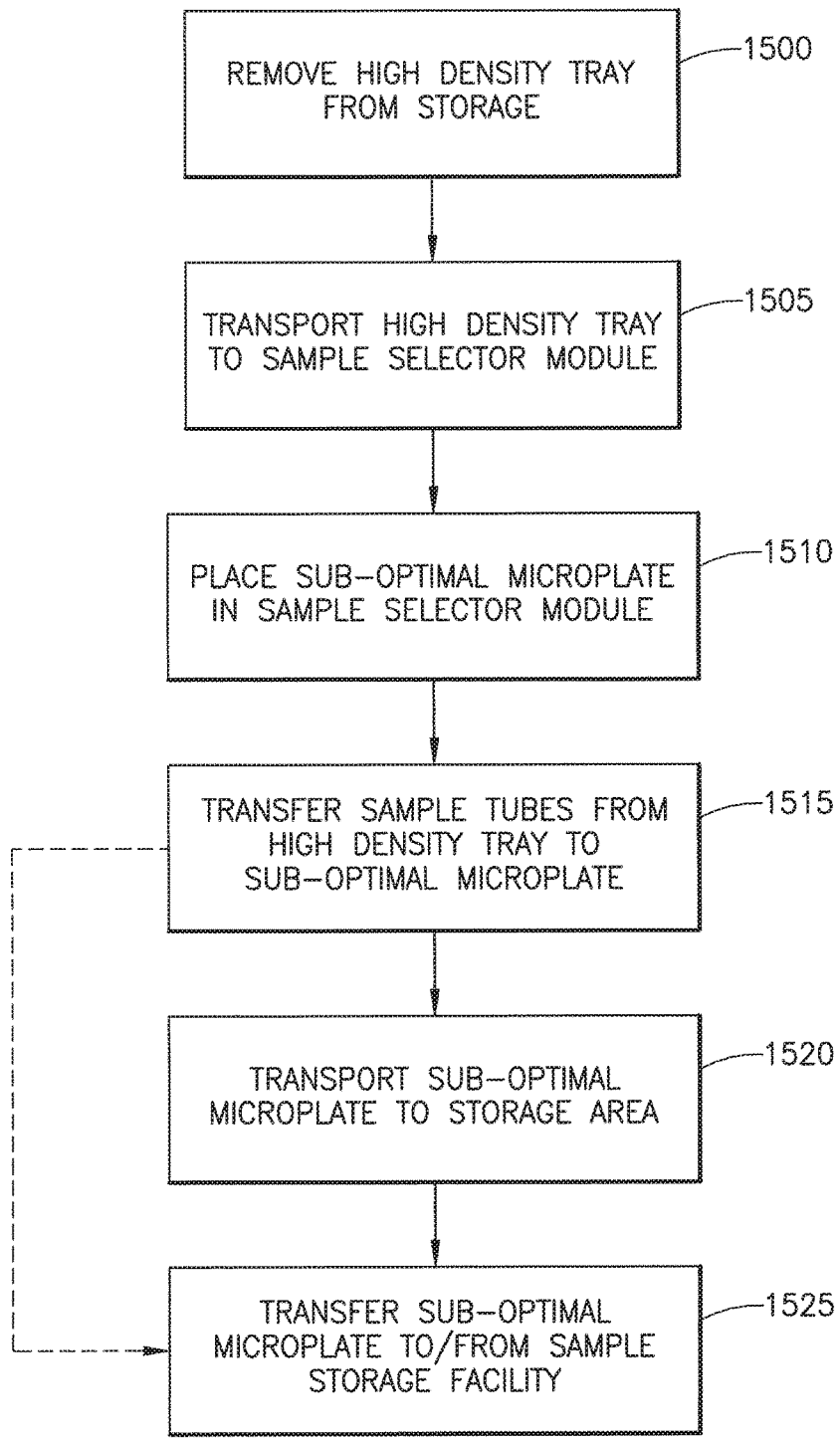
FIG. 5 is a flow chart in accordance with aspects of the disclosed embodiment.

Referring now to FIGS. 1A-1F, 2A, 2C and 5 an exemplary operation of the sample store facility 100, 100' will be described. In one aspect, the transport shuttle 112 picks or otherwise removes one or more high density trays 370 from one or more of the storage zones 110A, 110B (FIG. 5, Block 1500). The transport shuttle 112 transfers the one or more high density trays 370 to a sample selector module 190 and inserts the one or more high density tray 370 into one or more holding areas 300A-300C of the sample selector module 190 (FIG. 5, Block 1505). The transport shuttle 112 may also place a sub-optimal sample tube holding microplate 200 in one or more holding areas 300A-300C of the sample selector module 190 (FIG. 5, Block 1510), while in other aspects the microplate 200 may be placed within the sample selector module in any suitable manner. In one aspect, the at least one transfer arm portion 400A, for example, transfers one or more sample tubes 250 from the high density storage tray 370 of the automated sample storage facility 100, 100' to a sub-optimal sample tube holding microplate 200, of the sample storage facility 100, 100' (FIG. 5, Block 1515).

As noted above, the sub-optimal sample tube holding microplate 200 has a predetermined array 201 of tube holding receptacles 210 formed in a plate frame 200F, the tube holding receptacles 210 of the predetermined array 201 having a SBS standard pitch X corresponding to the predetermined array 201, and being configured for holding therein sample store and transport tubes 250, disposed for containing sample specimens in storage and effecting sample store and transport tube 250 delivery to a sample processing/preparation module 163, the predetermined array 201 of tube holding receptacles 210 defining a volume capacity of the tube holding microplate 200, and each of the tube holding receptacles 210 being shaped to conformally engage walls 251W of the sample store and transport tube 250 and hold the sample store and transport tube 250, wherein the tube holding receptacles 210 of the predetermined array 201 are arranged so that the tube holding microplate volume capacity defined by the predetermined array 201 of tube holding receptacles 210 is an under optimum volume capacity.

In one aspect, the high density trays 370 may be removed from the sample selector module 190 and replaced with different high density trays 370 for transferring additional sample tubes 250 to the microplate 200. In other aspects, the microplate 200 may be removed from the sample selector module 190 and transferred to a different sample selector module 190 for transferring additional sample tubes 250 to the sub-optimal microplate. In one aspect, the transfer shuttle 112 removes the microplate 200 from the sample selector module 190 and transfers the microplate to storage area 140 so that the sample selector module(s) 130 form part of a sample transport/picking chain or path between (e.g. to or from) the storage zones 110A, 110B and the sample storage area 140 formed by the sub-optimal microplates 200. In other aspects, the microplates 200 may be transferred by the transport shuttle 112 from the sample selector modules 130 to the input/output module 130.

In one aspect, the sample tubes 250, stored in the under optimum volume capacity tube holding microplate 200, are transferred from, for example, the storage area 140 into and out of the automated sample storage facility 100, 100' (FIG.

5, Block 1520). For example, in one aspect, the transport shuttle 112 may remove the microplate 200 from the sample selector module 190 and transfer the sample selector module 190 to the input/output module 130 (FIG. 5, Block 1525). In one aspect the transport shuttle 112 transfers the microplate 200 to the storage area 140 prior to transfer of the microplate 200 to the input/output module 130. The microplate 200 may be removed from the sample storage facility 100, 100' through the input/output module 130 in any suitable manner, such as with any suitable automation or by a human for transport of the microplate 200 to any suitable processing module such as sample processing/preparation module 163 such as those described herein.

Figure 6:
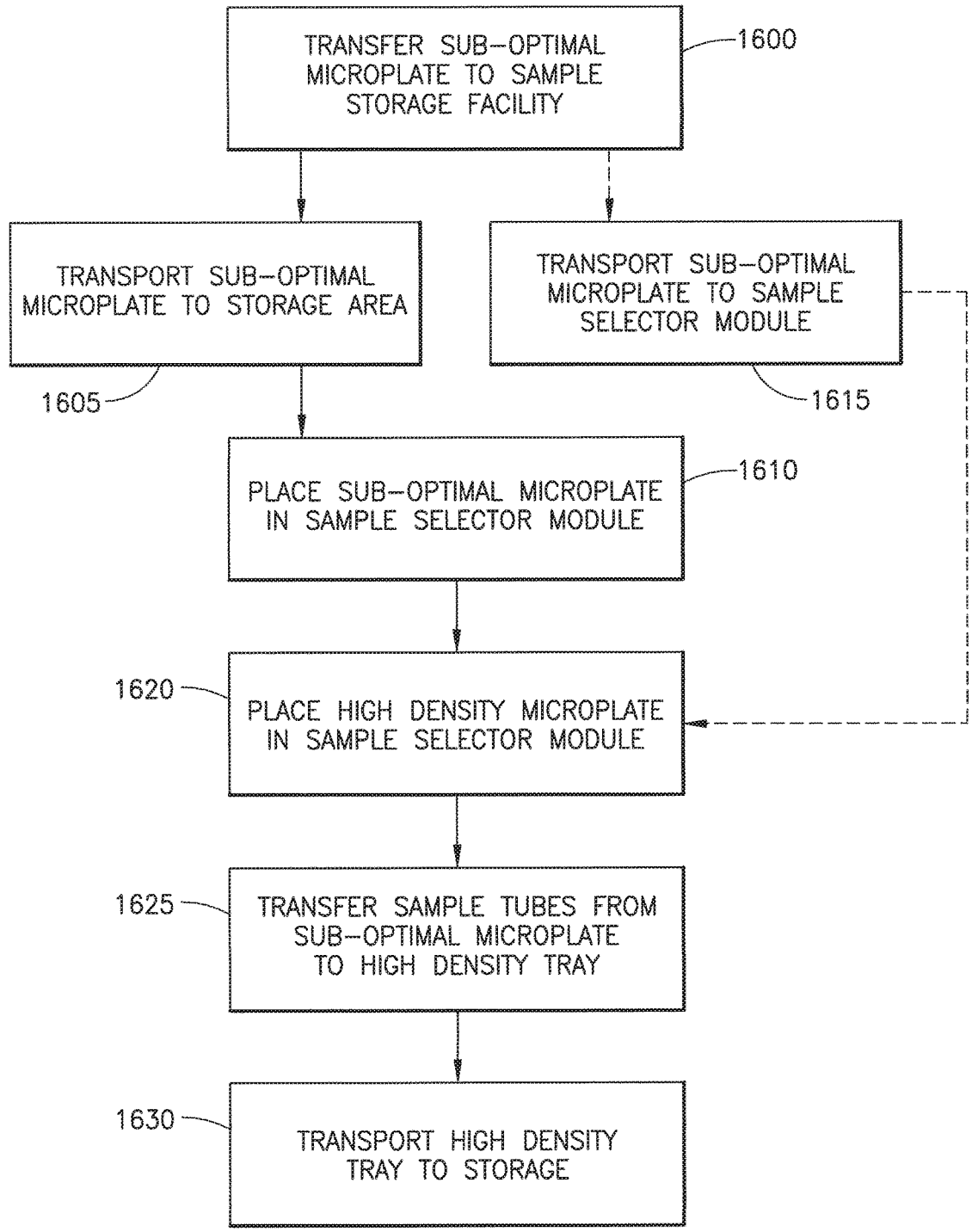
FIG. 6 is a flow chart in accordance with aspects of the disclosed embodiment.

Referring also to FIG. 6, sample tubes 250 may be input to the sample storage facility 100, 100' in a manner substantially opposite to that described above. For example, the sample tubes 250, containing samples, are placed on or otherwise pre-disposed in the microplate(s) 200. The microplate(s) 200 are transferred in any suitable manner, such as by e.g. automated or by human transport, to the input/output module 130 (FIG. 6, Block 1600). The transport shuttle 112 may remove the microplate(s) 200 from the input/output module 130 and in one aspect, transfers the microplate 200 to the storage area 140 (FIG. 6, Block 1605). The transport shuttle 112 may transport the microplate from the storage area 140 to the sample selector module 190 where, as above, the sample selector modules form part of a sample transport/picking chain or path between (e.g. to or from) the sample storage area 140 formed by the sub-optimal microplates 200 to the storage zones 110A, 110B (FIG. 6, Block 1610). In other aspects, the transport shuttle 112 transfers the microplate 200 from the input/output module 130 to the sample selector module 190 (FIG. 6, Block 1615).

In one aspect, the transport shuttle 112 inputs one or more high density trays 370 into holding areas 300A-300C of the sample selector module 190 (FIG. 6, Block 1620) where the sample tubes 250 are transferred from the microplate 200 to one more of the high density trays 370 as described above, such as in a efficient distribution (FIG. 6, Block 1625). The high density trays 370 are removed from the sample selector module 190 by the transport shuttle 112 and are transferred to the storage zones 110A, 110B (FIG. 6, Block 1630).

Figure 8:
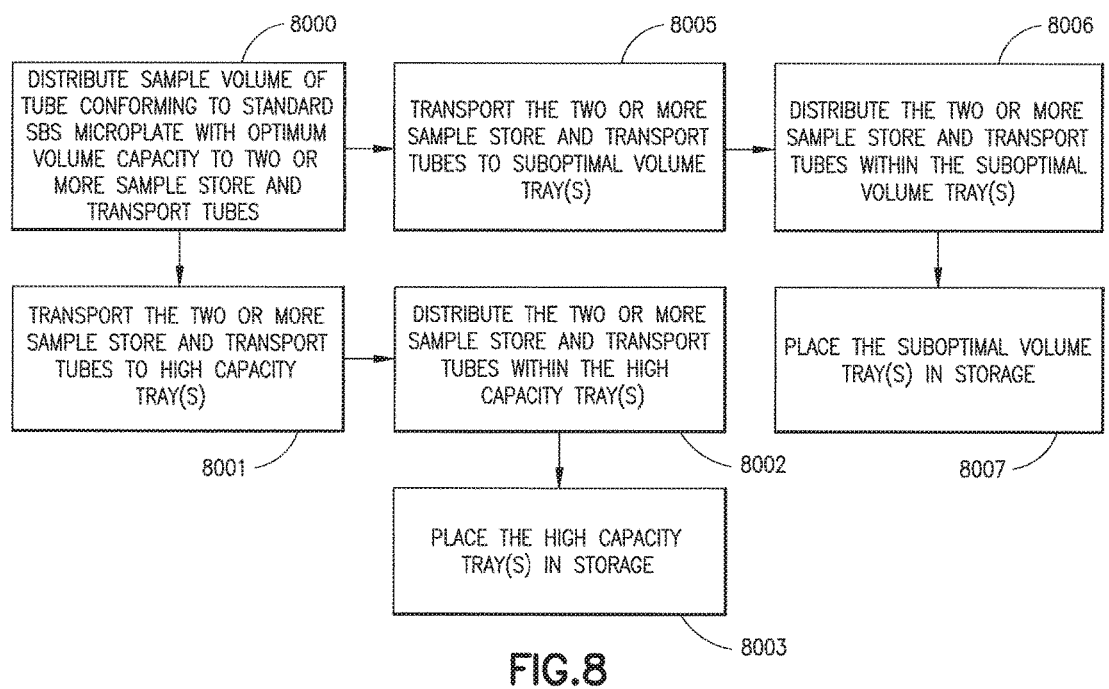
FIG. 8 is a flow diagram accordance with aspects of the disclosed embodiment.

In one aspect, referring to FIGS. 7 and 8, a predetermined sample specimen volume 2000V held in or otherwise corresponding to a conventional 9 mm sample tube 2000 is distributed to two or more sample store and transport tubes 250 so that each sample tube 250 holds a respective predetermined amount or portion 2000VA, 2000VB, 2000VC of the sample specimen volume 2000V so that any suitable number of copies of the sample held in the tube 2000 are created for placement in storage (FIG. 8, Block 8000). In one aspect, the two or more sample tubes 250 (e.g. copies of the sample obtained from the sample tube 2000) are placed in one or more high capacity trays 370 for being transported to storage, such as sample storage zones 110A, 110B, and (FIG. 8, Block 80001). In one aspect, the sample tubes 250 are distributed in the one or more high capacity trays 370 (by for example, one or more sample selector modules 190, 190') based on an optimum distribution or rules based weighted distribution of the associated sample tubes 250 or other suitable criteria (FIG. 8, Block 8002) as described herein. As also described herein, multiple copies of the sample obtained from a common tube 2000 may be placed in a common high capacity tray 370 so that an increased number of tubes including the sample from common tube 2000 are provided to the picker. The high capacity trays 370 are removed from, for example, the one or more sample selector modules 190, 190' by the transport 112 and transported in any suitable manner to one or more of the storage zones 110A, 110B for storage (FIG. 3, Block 8003). In another aspect, the two or more sample tubes 250 (e.g. copies of the sample obtained from the sample tube 2000) are placed in one or more sub-optimal volume trays 200 for being transported to storage, such as sample storage zones 110A, 110B, and (FIG. 8, Block 80005). In one aspect, the sample tubes 250 are distributed in the one or more sub-optimal volume trays 200 (by for example, one or more sample selector modules 190, 190') based on an optimum distribution or rules based weighted distribution of the associated sample tubes 250 or other suitable criteria, in a manner substantially similar to that described above with respect to the high capacity trays 370 (FIG. 8, Block 80006). As also described herein, multiple copies of the sample obtained from a common tube 2000 may be placed in a common sub-optimal volume tray 200 so that an increased number of tubes including the sample from common tube 2000 are provided to the picker. The sub-optimal volume trays 200 are removed from, for example, the one or more sample selector modules 190, 190' by the transport 112 and transported in any suitable manner to one or more of the storage zones 110A, 110B for storage (FIG. 8, Block 8007). As described above, in one aspect both the high capacity trays 370 and the sub-optimal volume trays 200 are stored in the storage areas 110A, 110B while in other aspects one of the high capacity trays 370 or the sub-optimal volume trays 200 are stored in the storage areas 110A, 110B. In still other aspects, high capacity trays 370 may be stored in one of storage areas 110A, 110B while sub-optimal volume trays 200 are stored in the other one of the storage areas 110A, 110B.

In accordance with one or more aspects of the disclosed embodiment an automated sample specimen storage system comprises: a tube holding microplate including a plate frame; a predetermined array of tube holding receptacles formed in the plate frame, the tube holding receptacles of the predetermined array having a SBS standard pitch corresponding to the predetermined array, and being configured for holding therein sample store and transport tubes, each disposed so as to contain sample specimen in a sample storage of the automated sample specimen storage system and to effect, with the sample store and transport tube, delivery from the sample storage to a workstation, the predetermined array of tube holding receptacles defining a volume capacity of the tube holding microplate; and each of the tube holding receptacles being shaped to engage walls of the sample store and transport tubes and hold a respective one of the sample store and transport tubes, wherein the tube holding receptacles of the predetermined array are arranged so that the tube holding microplate volume capacity defined by the predetermined array of tube holding receptacles is an under optimum volume capacity.

In accordance with one or more aspects of the disclosed embodiment the configuration of tube holding receptacles of the predetermined array is a suboptimal density with respect to a density of a standard SBS microplate standard pitch.

In accordance with one or more aspects of the disclosed embodiment the predetermined array of tube holding receptacles defines a storage array within the automated sample specimen storage system, for the sample store and transport tubes.

In accordance with one or more aspects of the disclosed embodiment the automated sample specimen storage system further comprises an automated storage an retrieval system configured for the automated storage and retrieval of sample store and transport tubes from the sample storage with a predetermined throughput capacity to the storage array, wherein the storage array is balanced with the predetermined throughput capacity of the automated storage and retrieval system so that the sub-optimal density of the predetermined array effects increased throughput of the sample store and transport tubes from the sample storage to the storage array relative to a storage area with optimal volume capacity arrayed tube holding receptacles.

In accordance with one or more aspects of the disclosed embodiment the storage array, and the automated storage and retrieval system are balanced so that the suboptimal density of the predetermined array effects increased throughput of the sample store and transport tubes from the sample storage to the storage array for a predetermined transfer action of the automated storage and retrieval system to the storage array relative to a storage area with optimal volume capacity arrayed tube holding receptacles.

In accordance with one or more aspects of the disclosed embodiment the automated sample specimen storage system further comprises: a storage zone configured for storing the sample store and transport tubes; and a sample selector module disposed between the storage zone and the storage array where the sample selector forms part of a sample transport and picking path between the storage zone and the storage array.

In accordance with one or more aspects of the disclosed embodiment the storage array is separate and distinct from a sample storage of the automated sample specimen storage system.

In accordance with one or more aspects of the disclosed embodiment the tube distribution and placement in the sample storage are balanced with the storage array so that the sample storage has a sample store and transport tube capacity that effects increased throughput of the sample store and transport tubes from the sample storage to the storage array relative to a storage area with optimal volume capacity arrayed tube holding receptacles.

In accordance with one or more aspects of the disclosed embodiment the automated sample specimen storage system further comprises: a high capacity sample storage tray that includes an array of tube holding receptacles having a capacity related to the under optimum volume capacity of the tube holding microplate with an optimized center to center pitch between tube holding receptacles; and a controller configured to effect storage of the sample store and transport tubes within the high density sample storage tray in an efficient distribution for the capacity the of the high capacity sample storage tray.

In accordance with one or more aspects of the disclosed embodiment the controller is configured so that the distribution of sample store and transport tubes and a capacity of the high density sample storage tray effects an increased pick rate in sample store and transport tube picking relative to a standard capacity of a high capacity tray and storage area with optimal volume capacity arrayed tube holding receptacles.

In accordance with one or more aspects of the disclosed embodiment a footprint of the plate frame and the SBS standard pitch are decoupled from a diameter of the sample store and transport tube.

In accordance with one or more aspects of the disclosed embodiment the automated sample specimen storage system further comprises: a housing having a sealed interior, the tube holding microplate being configured for transfer to and from the sealed interior to effect transfer of the sample store and transport tubes, held by the tube holding microplate, between the sealed interior and the workstation.

In accordance with one or more aspects of the disclosed embodiment the sample store and transport tubes each have a diameter of about 6 mm.

In accordance with one or more aspects of the disclosed embodiment the SBS standard pitch corresponding to the predetermined array is a pitch of about 9 mm.

In accordance with one or more aspects of the disclosed embodiment a method for storing sample specimens in an automated sample specimen storage system comprises: providing a tube holding microplate where the tube holding microplate includes a predetermined array of tube holding receptacles formed in a plate frame, the tube holding receptacles of the predetermined array having a SBS standard pitch corresponding to the predetermined array, and being configured for holding therein sample store and transport tubes, each disposed so as to contain sample specimen in a sample storage of the automated sample specimen storage system and to effect, with the sample store and transport tube, delivery to from the sample storage to a workstation, the predetermined array of tube holding receptacles defining a volume capacity of the tube holding microplate, and each of the tube holding receptacles being shaped to engage walls of a sample store and transport tube and hold a respective one of the sample store and transport tubes, wherein the tube holding receptacles of the predetermined array are arranged so that the tube holding microplate volume capacity defined by the predetermined array of tube holding receptacles is an under optimum volume capacity; and storing specimen within the sample store and transport tubes in the under optimum volume capacity tube holding microplate, within the automated sample specimen storage system and for transport into and out of the automated sample specimen storage system.

In accordance with one or more aspects of the disclosed embodiment the method further comprises transferring the sample store and transport tubes between a storage zone and the tube holding microplate through a sample selector module disposed along a path between the storage zone and a storage area formed by the tube holding microplate.

The method further comprises providing a high capacity sample storage tray that includes an array of tube holding receptacles having a capacity related to the under optimum volume capacity of the tube holding microplate with an optimized center to center pitch between tube holding receptacle, wherein the sample store and transport tubes are arranged in the high capacity sample storage tray in an optimized distribution for the capacity of the high capacity sample storage tray.

In accordance with one or more aspects of the disclosed embodiment the method further comprises transferring the sample store and transport tubes between the tube holding microplates and one or more high capacity storage trays with the sample selector module.

In accordance with one or more aspects of the disclosed embodiment the sample store and transport tubes are arranged in the one or more high capacity sample storage trays based on rules weighting or biasing tube storage distribution in the high capacity sample storage tray to place the sample store and transport tubes in associated positions within the one or more high capacity sample storage trays.

In accordance with one or more aspects the disclosed embodiment the sample store and transport tubes are arranged in the one or more high capacity storage trays so that a pick rate for picking the sample store and transport tubes from the high capacity storage trays is optimized for a given storage space of the sample storage of the automated sample specimen storage system based on the under optimum volume capacity of the tube holding microplate.

In accordance with one or more aspects of the disclosed embodiment the sample store and transport tubes are arranged in the one or more high capacity storage trays so that a pick rate for picking the sample store and transport tubes from the high capacity storage trays is optimized for a given transport motion of an automated storage and retrieval system moving the sample store and transport tubes within the automated sample specimen storage system based on the under optimum volume capacity of the tube holding microplate.

In accordance with one or more aspects of the disclosed embodiment a method comprises: transferring sample store and transport tubes from a high capacity storage tray of an automated storage system to a tube holding microplate interfacing with the automated storage system, the microplate having a predetermined array of tube holding receptacles formed in a plate frame, the tube holding receptacles of the predetermined array having a SBS standard pitch corresponding to the predetermined array, and being configured for holding therein the sample store and transport tubes, each disposed so as to contain sample specimen in a sample storage, of the automated storage system, for effecting, with the sample store and transport tube, delivery from the sample storage to a workstation, the predetermined array of tube holding receptacles defining a volume capacity of the tube holding microplate, and each of the tube holding receptacles being shaped to engage walls of and hold the sample store and transport tube, wherein the tube holding receptacles of the predetermined array are arranged so that the tube holding microplate volume capacity defined by the predetermined array of tube holding receptacles is an under optimum volume capacity; and transporting the tubes, stored the under optimum volume capacity tube holding microplate, into and out of the automated storage system.

In accordance with one or more aspects of the disclosed embodiment the method further comprises transferring the sample store and transport tubes between the high capacity storage tray and the tube holding microplate through a sample selector module disposed along a path between a storage zone of the automated storage system and a storage area formed by the tube holding microplate.

In accordance with one or more aspects of the disclosed embodiment the sample store and transport tubes are arranged in the high capacity storage tray in an optimized distribution for the capacity of the high capacity storage tray.

In accordance with one or more aspects of the disclosed embodiment the sample store and transport tubes are arranged in the high capacity storage tray based on rules weighting or biasing tube storage distribution in the high capacity storage tray to place the sample store and transport tubes in associated positions within the one or more high capacity storage trays.

In accordance with one or more aspects of the disclosed embodiment the sample store and transport tubes are arranged in the one or more high capacity storage trays so that a pick rate for picking the sample store an transport tubes from the high capacity storage trays is optimized for a given storage space of the sample storage of the automated storage system based on the under optimum volume capacity of the tube holding microplate.

In accordance with one or more aspects of the disclosed embodiment the sample store and transport tubes are arranged in the high capacity storage tray so that a pick rate for picking the sample store and transport tubes from the high capacity storage tray is optimized for a given transport motion of an automated storage and retrieval system moving the sample store and transport tubes within the automated storage system based on the under optimum volume capacity of the tube holding microplate.

In accordance with one or more aspects of the disclosed embodiment a predetermined sample specimen volume corresponding to a 9 mm diameter sample tube is distributed to two or more sample store and transport tubes and distributed sample storage based on an optimized distribution or rules based weighted distribution of the associated sample store and transport tubes.

In accordance with one or more aspects of the disclosed embodiment an automated sample specimen storage system comprises: a tube holding microplate including a plate frame; a predetermined array of tube holding receptacles formed in the plate frame, the tube holding receptacles of the predetermined array having a pitch from about 8 mm to about 10 mm and a web wall thickness of at least about 1 mm, and being configured for holding therein sample store and transport tubes, each disposed so as to contain sample specimen in a sample storage of the automated sample specimen storage system and to effect, with the sample store and transport tube, delivery from the sample storage to a workstation, the predetermined array of tube holding receptacles defining a volume capacity of the tube holding microplate; and each of the tube holding receptacles being shaped to engage walls of the sample store and transport tubes and hold a respective one of the sample store and transport tubes, wherein the tube holding receptacles of the predetermined array are arranged so that the tube holding microplate volume capacity defined by the predetermined array of tube holding receptacles is an under optimum volume capacity.

In accordance with one or more aspects of the disclosed embodiment the configuration of tube holding receptacles of the predetermined array is a suboptimal density with respect to a density of a microplate with an SBS standard footprint dimension and holding receptacle to web wall thickness ratio for optimum array volume capacity.

In accordance with one or more aspects of the disclosed embodiment the web wall thickness is greater than about 1 mm to about 3 mm.

In accordance with one or more aspects of the disclosed embodiment an automated sample specimen storage system comprises: a tube holding microplate including a plate frame; a predetermined array of tube holding receptacles formed in the plate frame, the tube holding of the predetermined array having a pitch between centers of the tube holding receptacles and a web wall thickness between the receptacles where the web wall thickness is at least greater than about 10% of the pitch, and being configured for holding therein sample store and transport tubes, each disposed so as to contain sample specimen in a sample storage of the automated sample specimen storage system and to effect, with the sample store and transport tube, delivery from the sample storage to a workstation, the predetermined array of tube holding receptacles defining a volume capacity of the tube holding microplate; and each of the tube holding receptacles being shaped to engage walls of the sample store and transport tubes and hold a respective one of the sample store and transport tubes, wherein the tube holding receptacles of the predetermined array are arranged so that the tube holding microplate volume capacity defined by the predetermined array of tube holding receptacles is an under optimum volume capacity.

In accordance with one or more aspects of the disclosed embodiment a method for storing sample specimens in an automated sample specimen storage system comprises: providing a tube holding microplate including a plate frame, and a predetermined array of tube holding receptacles formed in the plate frame, the tube holding receptacles of the predetermined array having a pitch from about 8 mm to about 10 mm and a web wall thickness of at least about 1 mm, and being configured for holding therein sample store and transport tubes, each disposed so as to contain sample specimen in a sample storage of the automated sample specimen storage system, where each of the tube holding receptacles being shaped to engage walls of the sample store and transport tubes and hold a respective one of the sample store and transport tubes; and effecting, with the sample store and transport tube, delivery from the sample storage to a workstation, where the predetermined array of tube holding receptacles define a volume capacity of the tube holding microplate; wherein the tube holding receptacles of the predetermined array are arranged so that a tube holding microplate volume capacity defined by the predetermined array of tube holding receptacles is an under optimum volume capacity.

In accordance with one or more aspects of the disclosed embodiment the configuration of tube holding receptacles of the predetermined array is a suboptimal density with respect to a density of a microplate with an SBS standard footprint dimension and holding receptacle to web wall thickness ratio for optimum array volume capacity.

In accordance with one or more aspects of the disclosed embodiment the web wall thickness is greater than about 1 mm to about 3 mm.

In accordance with one or more aspects of the disclosed embodiment a method for storing sample specimens in an automated sample specimen storage system comprises: providing a tube holding microplate including a plate frame, and a predetermined array of tube holding receptacles formed in the plate frame, the tube holding receptacles of the predetermined array having a pitch between centers of the tube holding receptacles and web wall thickness between the receptacles where the web wall thickness is at least greater than about 10% of the pitch, and being configured for holding therein sample store and transport tubes, each disposed so as to contain sample specimen in a sample storage of the automated sample specimen storage system, each of the tube holding receptacles being shaped to engage walls of the sample store and transport tubes and hold a respective one of the sample store and transport tubes; and effecting, with the sample store and transport tube, delivery from the sample storage to a workstation, where the predetermined array of tube holding receptacles define a volume capacity of the tube holding microplate; wherein the tube holding receptacles of the predetermined array are arranged so that a tube holding microplate volume capacity defined by the predetermined array of tube holding receptacles is an under optimum volume capacity.

It should be understood that the foregoing description is only illustrative of the aspects of the disclosed embodiment. Various alternatives and modifications can be devised by those skilled in the art without departing from the aspects of the disclosed embodiment. Accordingly the aspects of the disclosed embodiment are intended to embrace all such alternatives, modifications and variances that fall within the scope of the appended claims. Further, the mere fact that different features are recited in mutually different dependent or independent claims does not indicate that a combination of these features cannot be advantageous used, such a combination remaining within the scope of the aspects of the invention.

What is claimed is:

1. An automated sample specimen storage system comprising:
    a tube holding microplate including
        a plate frame;
        a predetermined array of tube holding receptacles formed in the plate frame, the tube holding receptacles of the predetermined array having a SBS standard pitch corresponding to the predetermined array, and being configured for holding therein sample store and transport tubes that are separate and distinct from the predetermined array of tube holding receptacles, each tube holding receptacle being disposed so as to contain sample specimen in a sample storage array, of the automated sample specimen storage system and to effect, with the sample store and transport tube, delivery of the sample specimen from the sample storage array to a workstation, the predetermined array of tube holding receptacles defining a volume capacity of the tube holding microplate;
        each of the tube holding receptacles being shaped to engage walls of the sample store and transport tubes and hold a respective one of the sample store and transport tubes, wherein the tube holding receptacles of the predetermined array are sized and spaced from one another so that the tube holding microplate volume capacity defined by the predetermined array of tube holding receptacles is an under optimum volume capacity; and
    an automated storage and retrieval system configured for the automated storage and retrieval of sample store and transport tubes from a sample storage with a predetermined throughput capacity to the sample storage array, wherein the sample storage array is balanced with the predetermined throughput capacity of the automated storage and retrieval system so that the sub-optimal density of the predetermined array effects increased throughput of the sample store and transport tubes from the sample storage to the sample storage array relative to a storage area with optimal volume capacity arrayed tube holding receptacles.

2. The automated sample specimen storage system of claim 1, wherein the configuration of tube holding receptacles of the predetermined array is a suboptimal density with respect to a density of a standard SBS microplate standard pitch.

3. The automated sample specimen storage system of claim 1, wherein the predetermined array of tube holding receptacles defines the sample storage array within the automated sample specimen storage system, for the sample store and transport tubes.

4. The automated sample specimen storage system of claim 3, wherein the sample storage array and the automated storage and retrieval system are balanced so that the sub-optimal density of the predetermined array effects increased throughput of the sample store and transport tubes from the sample storage to the storage array for a predetermined transfer action of the automated storage and retrieval system to the storage array relative to a storage area with optimal volume capacity arrayed tube holding receptacles.

5. The automated sample specimen storage system of claim 4, further comprising:
   a storage zone configured for storing the sample store and transport tubes; and
   a sample selector module disposed between the storage zone and the storage array where the sample selector forms part of a sample transport and picking path between the storage zone and the storage array.

6. The automated sample specimen storage system of claim 3, wherein the storage array is separate and distinct from a sample storage of the automated sample specimen storage system.

7. The automated sample specimen storage system of claim 6, wherein the tube distribution and placement in the sample storage are balanced with the storage array so that the sample storage has a sample store and transport tube capacity that effects increased throughput of the sample store and transport tubes from the sample storage to the storage array relative to a storage area with optimal volume capacity arrayed tube holding receptacles.

8. The automated sample specimen storage system of claim 1, further comprising:
   a high capacity sample storage tray that includes an array of tube holding receptacles having a capacity related to the under optimum volume capacity of the tube holding microplate with an optimized center to center pitch between tube holding receptacles; and
   a controller configured to effect storage of the sample store and transport tubes within the high capacity sample storage tray in an efficient distribution for the capacity of the high capacity sample storage tray.

9. The automated sample specimen storage system of claim 8, wherein the controller is configured so that the distribution of sample store and transport tubes and a capacity of the high density sample storage tray effects an increased pick rate in sample store and transport tube picking relative to a standard capacity of a high capacity tray and storage area with optimal volume capacity arrayed tube holding receptacles.

10. The automated sample specimen storage system of claim 1, wherein a footprint of the plate frame and the SBS standard pitch are decoupled from a diameter of the sample store and transport tube.

11. The automated sample specimen storage system of claim 1, further comprising:
   a housing having a sealed interior, the tube holding microplate being configured for transfer to and from the sealed interior to effect transfer of the sample store and transport tubes, held by the tube holding microplate, between the sealed interior and the workstation.

12. The automated sample specimen storage system of claim 1, wherein the sample store and transport tubes each have a diameter of about 6 mm.

13. The automated sample specimen storage system of claim 1, wherein the SBS standard pitch corresponding to the predetermined array is a pitch of about 9 mm.

14. A method for storing sample specimens in an automated sample specimen storage system, the method comprising:
   providing a tube holding microplate where the tube holding microplate includes
      a predetermined array of tube holding receptacles formed in a plate frame, the tube holding receptacles of the predetermined array having a SBS standard pitch corresponding to the predetermined array, and being configured for holding therein sample store and transport tubes that are separate and distinct from the predetermined array of tube holding receptacles, each tube holding receptacle being disposed so as to contain sample specimen in a sample storage of the automated sample specimen storage system and to effect, with the sample store and transport tube, delivery of the sample specimen from the sample storage array to a workstation, the predetermined array of tube holding receptacles defining a volume capacity of the tube holding microplate, and
      each of the tube holding receptacles being shaped to engage walls of a sample store and transport tube and hold a respective one of the sample store and transport tubes, wherein the tube holding receptacles of the predetermined array are sized and spaced from one another so that the tube holding microplate volume capacity defined by the predetermined array of tube holding receptacles is an under optimum volume capacity;
   storing specimen within the sample store and transport tubes in the under optimum volume capacity tube holding microplate, within the automated sample specimen storage system and for transport into and out of the automated sample specimen storage system;
   providing an automated storage and retrieval system configured for the automated storage and retrieval of sample store and transport tubes from a sample storage with a predetermined throughput capacity to a sample storage array; and
   balancing the sample storage array with the predetermined throughput capacity of the automated storage and retrieval system so that the sub-optimal density of the predetermined array effects increased throughput of the sample store and transport tubes from the sample storage to the sample storage array relative to a storage area with optimal volume capacity arrayed tube holding receptacles.

15. The method of claim 14, further comprising transferring the sample store and transport tubes between a storage zone and the tube holding microplate through a sample selector module disposed along a path between the storage zone and a storage area formed by the tube holding microplate.

16. The method of claim 14, further comprising providing a high capacity sample storage tray that includes an array of tube holding receptacles having a capacity related to the under optimum volume capacity of the tube holding microplate with an optimized center to center pitch between tube holding receptacles, wherein the sample store and transport tubes are arranged in the high capacity sample storage tray in an optimized distribution for the capacity of the high capacity sample storage tray.

17. A method for transferring sample specimens in an automated sample specimen storage system, the method comprising:
   transferring sample store and transport tubes from a high capacity storage tray of an automated storage system to a tube holding microplate interfacing with the automated storage system, the microplate having
      a predetermined array of tube holding receptacles formed in a plate frame, the tube holding receptacles of the predetermined array having a SBS standard pitch corresponding to the predetermined array, and being configured for holding therein the sample store and transport tubes that are separate and distinct from the predetermined array of tube holding receptacles, each tube holding receptacle being disposed so as to contain sample specimen in a sample storage array, of the automated storage system, for effecting, with the sample store and transport tube, delivery of the sample specimen from the sample storage array to a workstation, the predetermined array of tube holding receptacles defining a volume capacity of the tube holding microplate, and each of the tube holding receptacles being shaped to engage walls of and hold the sample store and transport tube, wherein the tube holding receptacles of the predetermined array are sized and spaced from one another so that the tube holding microplate volume capacity defined by the predetermined array of tube holding receptacles is an under optimum volume capacity;

transporting the tubes, stored the under optimum volume capacity tube holding microplate, into and out of the automated storage system; and wherein the sample storage array of the automated storage system is balanced with a predetermined throughput capacity of the automated storage system so that a sub-optimal density of the predetermined array effects increased throughput of the sample store and transport tubes from a sample storage of the automated storage system to the sample storage array relative to a storage area with optimal volume capacity arrayed tube holding receptacles.

18. The method of claim 17, the method further comprising transferring the sample store and transport tubes between the high capacity storage tray and the tube holding microplate through a sample selector module disposed along a path between a storage zone of the automated storage system and a storage area formed by the tube holding microplate.

19. The method of claim 17, wherein the sample store and transport tubes are arranged in the high capacity storage tray in an optimized distribution for the capacity of the high capacity storage tray.

* * * * *